(12) United States Patent
Tybinkowski et al.

(10) Patent No.: US 7,396,160 B2
(45) Date of Patent: Jul. 8, 2008

(54) COMPUTERIZED TOMOGRAPHY (CT) IMAGING SYSTEM WITH MONOBLOCK X-RAY TUBE ASSEMBLY

(75) Inventors: Andrew P. Tybinkowski, Boxford, MA (US); Lidia Nemirovsky, Salem, MA (US); Eric M. Bailey, Danvers, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

(21) Appl. No.: 11/399,283

(22) Filed: Apr. 6, 2006

(65) Prior Publication Data

US 2006/0251218 A1    Nov. 9, 2006

Related U.S. Application Data

(63) Continuation-in-part of application No. 11/193,941, filed on Jul. 29, 2005, now Pat. No. 7,175,347.

(60) Provisional application No. 60/670,164, filed on Apr. 11, 2005, provisional application No. 60/593,001, filed on Jul. 30, 2004.

(51) Int. Cl.
*H01J 35/12* (2006.01)
*G21K 1/02* (2006.01)

(52) U.S. Cl. .................................. 378/199; 378/147

(58) Field of Classification Search .................. 378/4, 378/9, 19, 119, 127, 141, 142, 199, 200, 378/147–153

See application file for complete search history.

(56) References Cited

U.S. PATENT DOCUMENTS

| | | | |
|---|---|---|---|
| 3,603,975 A | | 9/1971 | Gordon |
| 4,870,671 A | * | 9/1989 | Hershyn ..................... 378/124 |
| 5,887,047 A | | 3/1999 | Bailey et al. |
| 5,982,843 A | | 11/1999 | Bailey et al. |
| 6,108,396 A | | 8/2000 | Bechwati et al. |
| 6,256,404 B1 | | 7/2001 | Gordon et al. |
| 6,285,028 B1 | | 9/2001 | Yamakawa |
| 6,396,902 B2 | | 5/2002 | Tybinkowski et al. |
| 6,459,767 B1 | * | 10/2002 | Boyer ........................ 378/121 |
| 6,522,721 B1 | * | 2/2003 | Lustberg ..................... 378/143 |
| 6,813,374 B1 | | 11/2004 | Karimi et al. |
| 6,857,778 B2 | | 2/2005 | Mun et al. |
| 7,175,347 B2 | | 2/2007 | Tybinkowski et al. |

\* cited by examiner

*Primary Examiner*—Irakli Kiknadze
(74) *Attorney, Agent, or Firm*—Pandiscio & Pandiscio

(57) ABSTRACT

A system for cooling an X-ray tube in a CT machine comprising a heat sink for drawing heat away from the X-ray tube and a collimator connected to the heat sink and adapted to collimate the X-rays emitted by the X-ray tube and "focus" those X-rays on an X-ray detector, the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

22 Claims, 25 Drawing Sheets

000
COMPUTERIZED TOMOGRAPHY (CT) IMAGING SYSTEM WITH MONOBLOCK X-RAY TUBE ASSEMBLY

REFERENCE TO PENDING PRIOR PATENT APPLICATION

This patent application is a continuation-in-part of prior U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE DRIVE, which patent application in turn claims benefit of: (i) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE; and (ii) prior U.S. Provisional Patent Application Ser. No. 60/593,001, filed Jul. 30, 2004 by Bernard Gordon et al. for ANATOMICAL SCANNING SYSTEM.

The three above-identified patent applications are hereby incorporated herein by reference.

FIELD OF THE INVENTION

This invention relates to anatomical imaging systems in general, and more particularly to Computerized Tomography (CT) imaging systems.

BACKGROUND OF THE INVENTION

Strokes are the third leading cause of death in the United States, causing approximately 177,000 deaths per year, and strokes are the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke). Computerized Tomography (CT) has emerged as the key imaging modality in the diagnosis of strokes. CT scanners generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning, including non-enhanced CT scanning, CT angiography scanning and CT perfusion scanning, is able to provide substantially all of the information needed to effectively diagnose (and hence properly treat) a stroke.

Unfortunately, in practice, the CT machine is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient.

Thus, there is an urgent need for a new and improved CT machine which is particularly well suited for use in stroke applications. More particularly, there is an urgent need for a small, mobile CT machine which can be pre-positioned in the emergency room and moved to the patient so that the patient can be scanned at their current location, thus effectively eliminating "round-trip" delays and dramatically reducing the time needed to properly diagnose the patient. It is also important that the CT machine be relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

In this respect it should also be appreciated that CT scanners utilize X-ray tubes to generate the X-rays that are used to scan the patient. These X-ray tubes typically produce a substantial amount of heat when generating their X-rays, and this heat must generally be dissipated in order to improve image quality and increase component life. However, it can be troublesome to dissipate this heat, particularly inasmuch as the X-ray tube: (i) is encapsulated by the scanner housing, which tends to trap the heat from the X-ray tube; (ii) is generally in close proximity to many other internal scanner components, which can also trap heat; and (iii) must keep at least the emitter portion of the X-ray tube exposed, in order to permit the X-rays to exit the tube and pass into the patient. Such considerations have generally resulted in relatively complex X-ray tube assemblies comprising the X-ray tube and its associated cooling system, which can add to scanner size, weight and cost. This is particularly true inasmuch as the X-ray tubes (and hence their associated cooling systems) are generally mounted on large rotating drums which move the X-ray tubes concentrically about the patient so as to achieve the necessary scanning angles; such rotational mounting generally complicates the delivery of power and/or fluids to the X-ray tube's cooling system.

Thus, there is a need for a new and improved approach for cooling the X-ray tube in a CT scanner, so as to help reduce the overall size, weight and cost of the CT scanner.

SUMMARY OF THE INVENTION

In accordance with the present invention, there is provided a novel system for cooling the X-ray tube in a CT scanner, wherein the novel system facilitates a reduction in the size, weight and cost of the CT scanner.

And there is provided a novel X-ray tube assembly for use in a CT scanner, wherein the novel X-ray tube assembly comprises an X-ray tube and its associated cooling system, and further wherein the novel X-ray tube assembly is relatively compact, lightweight and inexpensive.

And there is provided a novel CT machine incorporating the novel X-ray tube assembly, wherein the novel CT machine is relatively small, mobile and inexpensive.

In one form of the invention, there is provided a system for cooling an X-ray tube in a CT machine, wherein the X-ray tube is of the type comprising a rear cylindrical portion, a front cylindrical portion, an annular face formed at the intersection of the rear cylindrical portion and the front cylindrical portion, and an emitter opening formed in the front cylindrical portion for emitting X-rays from the X-ray tube, the system comprising:

a heat sink for drawing heat away from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;

the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

In another form of the invention, there is provided an X-ray tube assembly comprising:

an X-ray tube comprising:
a rear cylindrical portion;
a front cylindrical portion;
an annular face formed at the intersection of the rear cylindrical portion and the front cylindrical portion; and
an emitter opening formed in the front cylindrical portion for emitting X-rays from the X-ray tube; and a system for cooling the X-ray tube in a CT machine, the system comprising:
a heat sink for drawing heat away from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and
a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;
the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

In another form of the invention, there is provided an anatomical imaging system comprising:

a CT machine; and
a transport mechanism mounted to the base of the CT machine, wherein the transport mechanism comprises a fine movement mechanism for moving the CT machine precisely, relative to the patient, during scanning;
wherein the CT machine comprises:
an X-ray tube assembly comprising:
an X-ray tube comprising:
a rear cylindrical portion;
a front cylindrical portion;
an annular face formed at the intersection of the rear cylindrical portion and the front cylindrical portion; and
an emitter opening formed in the front cylindrical portion for emitting X-rays from the X-ray tube; and
a system for cooling the X-ray tube in a CT machine, the system comprising:
a heat sink for drawing heat away from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and
a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;
the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

CT Machine 5 In General

Figure 1:
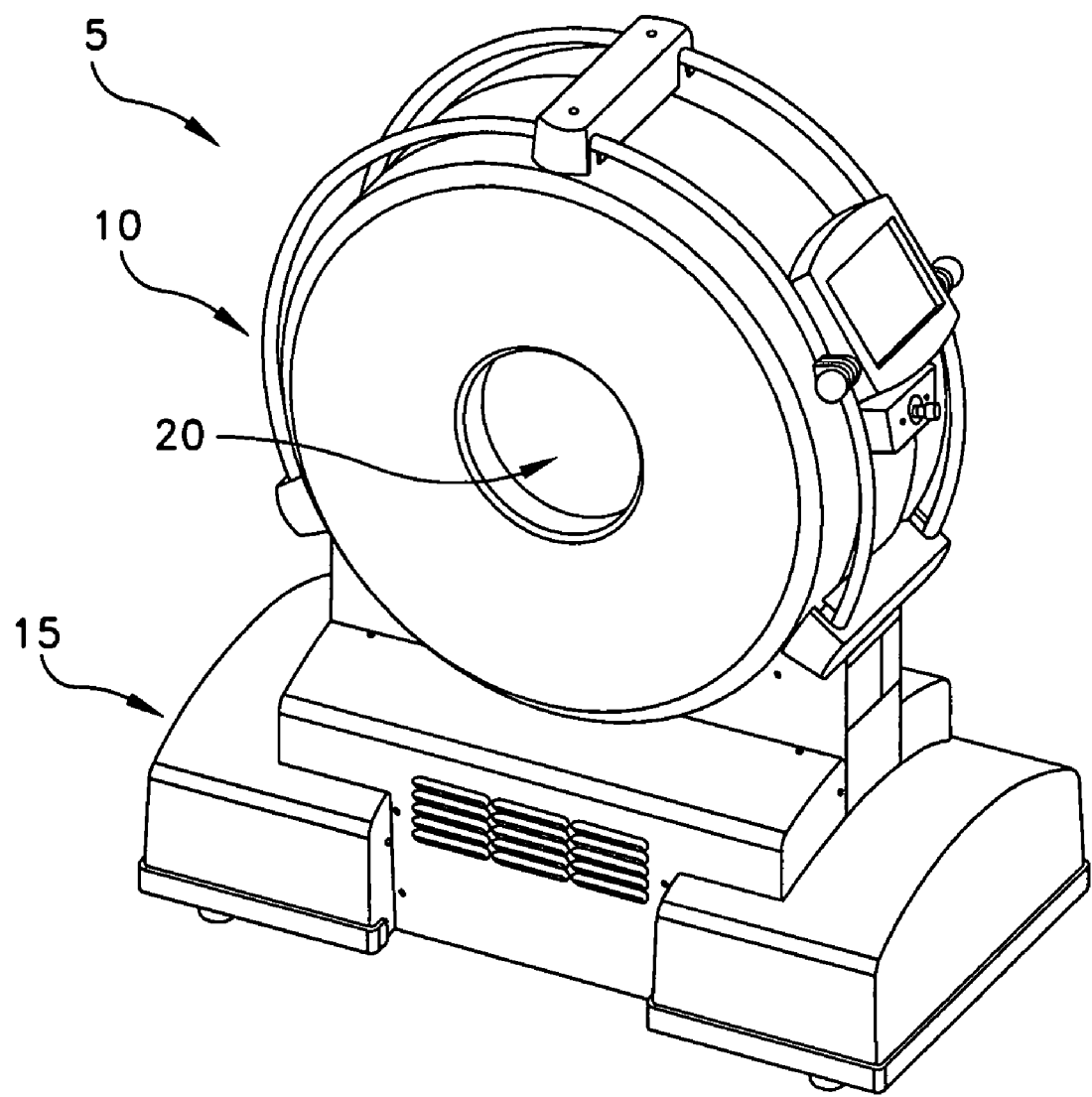
FIGS. 1 and 2 are schematic external views of a novel CT machine formed in accordance with the present invention.
Figure 2:
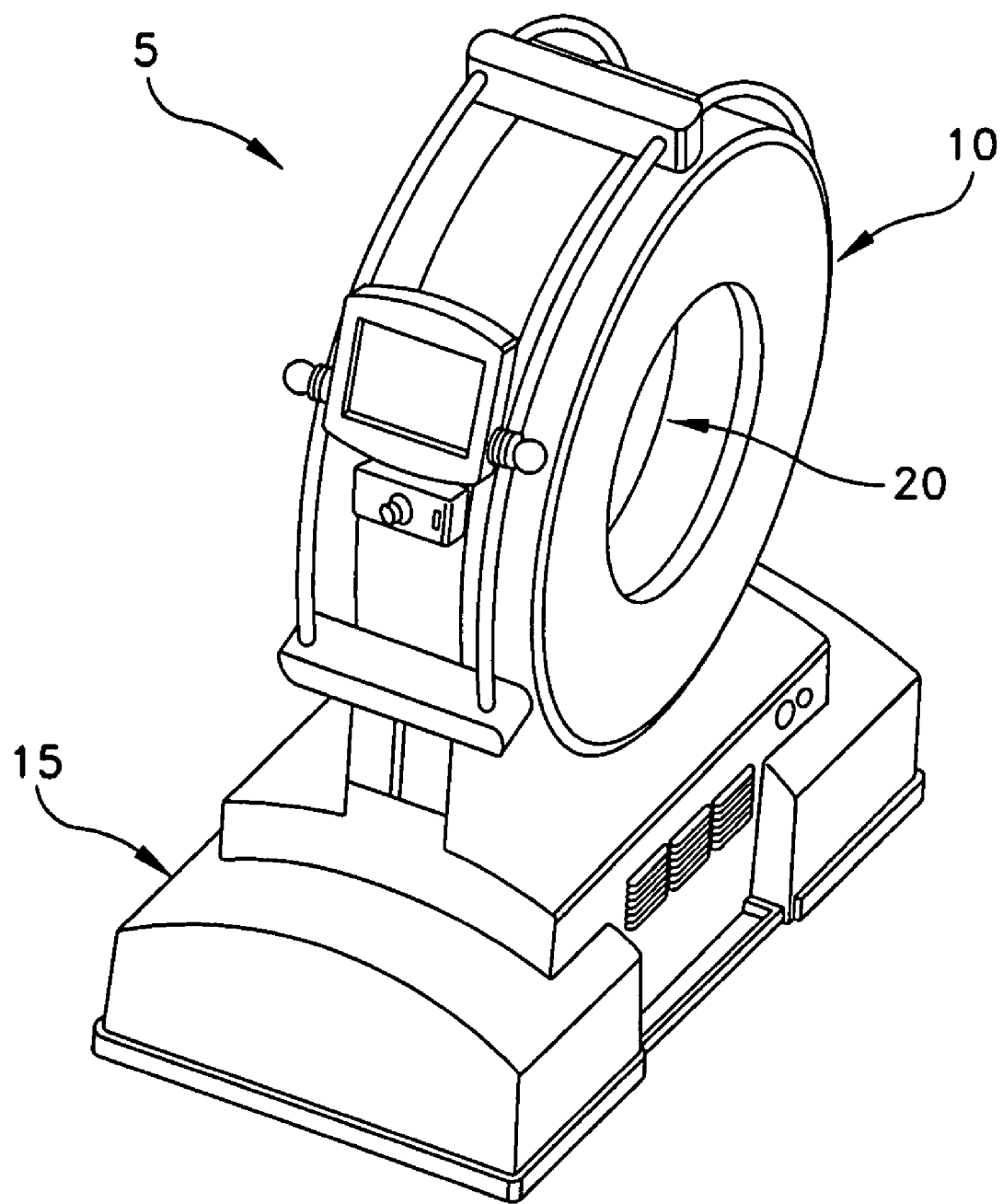

Looking first at FIGS. 1 and 2, there is shown a novel CT machine 5 formed in accordance with the present invention. CT machine 5 generally comprises a torus 10 which is supported by a base 15. A center opening 20 is formed in torus 10. Center opening 20 receives the patient anatomy which is to be scanned, i.e., the head of the patient when CT machine 5 is to be used in stroke applications.

Figure 3:
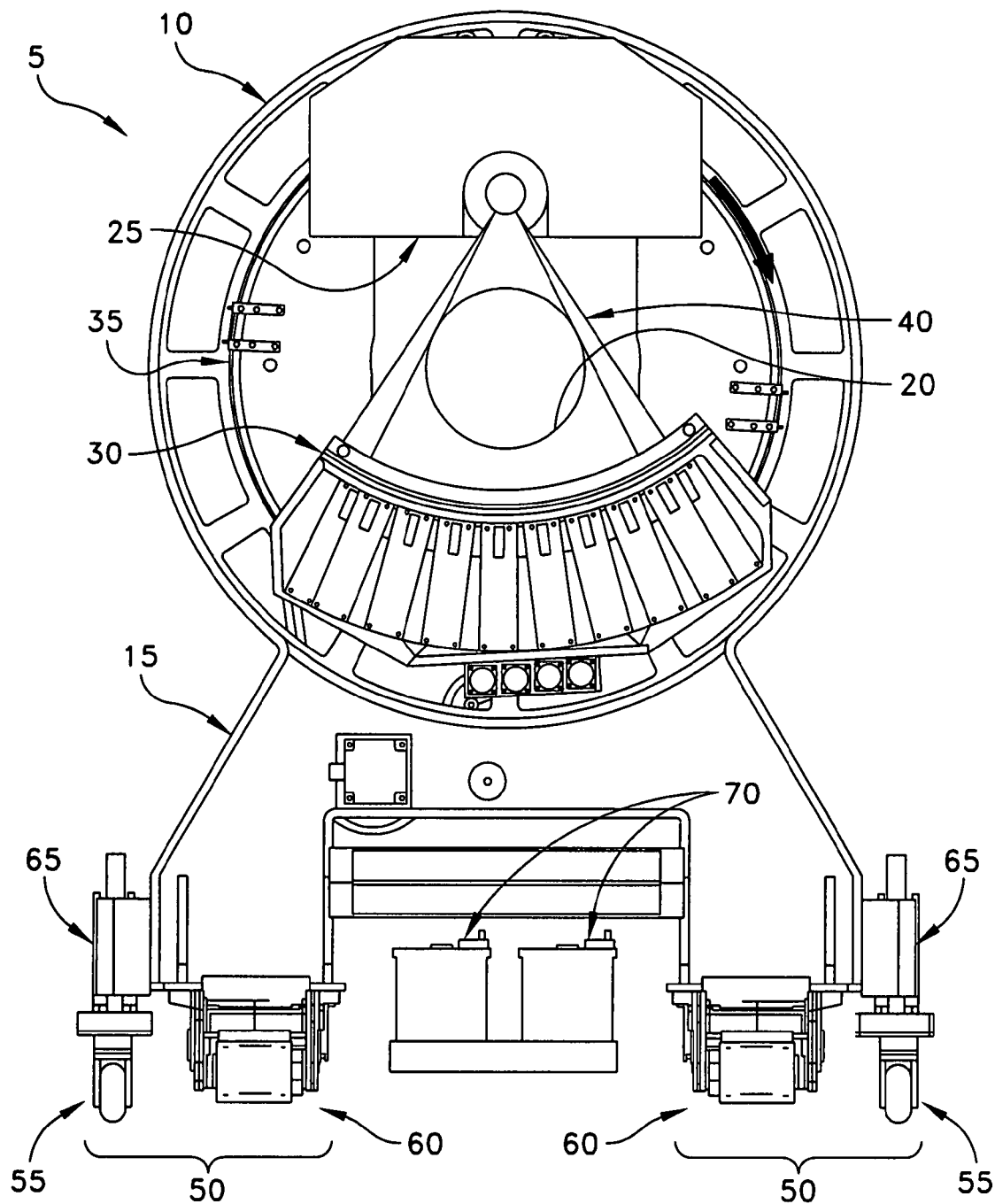
FIG. 3 is a schematic internal view of the novel CT machine shown in FIGS. 1 and 2.

Looking next at FIG. 3, torus 10 generally comprises a X-ray tube assembly 25, an X-ray detector assembly 30, and a rotating drum assembly 35. X-ray tube assembly 25 and X-ray detector assembly 30 are mounted to the rotating drum assembly 35 in diametrically-opposing relation, such that the X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on the rotating drum assembly 35 so that they are rotated concentrically about center opening 20, the X-ray beam 40 will be passed through the patient's anatomy along a full range of radial positions, so as to enable the CT machine to create the desired computer model of the scanned anatomy.

The various electronic hardware and software for controlling the operation of X-ray tube assembly 25, X-ray detector assembly 30, and rotating drum assembly 35, as well as for processing the acquired scan data so as to generate the desired computer model, may be of the sort well known in the art and may be located in torus 10 and/or base 15.

Still looking now at FIG. 3, base 15 comprises a transport assembly 50 for moving the CT machine 5 about relative to the patient. More particularly, as disclosed in the aforementioned U.S. patent application Ser. No. 11/193,941, which patent application is hereby incorporated herein by reference, transport assembly 50 comprises a gross movement mechanism 55 for moving CT machine 5 relatively quickly across room distances, and a fine movement mechanism 60 for moving the CT machine precisely, relative to the patient, during scanning. As discussed in detail in the aforementioned U.S. patent application Ser. No. 11/193,941, gross movement mechanism 55 preferably comprises a plurality of casters, and fine movement mechanism 60 preferably comprises a plurality of centipede belt drives. Hydraulic apparatus 65 permits either gross movement mechanism 55 or fine movement mechanism 60 to be engaged with the floor, whereby to facilitate appropriate movement of the CT machine 5.

Base 15 preferably also includes other system components in addition to those discussed above, e.g., batteries 70 for powering the electrical components of CT machine 5, etc.

The various components of CT machine 5 are engineered so as to provide a relatively small, mobile and inexpensive CT machine. Among other things, and as will hereinafter be discussed in further detail, X-ray tube assembly 25 is engineered so as to be relatively compact, lightweight and inexpensive.

CT machine 5 is particularly well suited for use in stroke applications. More particularly, CT machine 5 is a small, mobile unit which can be pre-positioned in the emergency room and moved to the patient so that the patient can be scanned at their current location, thus eliminating delays due to patient transport and thereby dramatically reducing the time needed to properly diagnose the patient. In addition, the CT machine 5 is relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

Thus, the mobile CT machine 5 can be located in the emergency room of a hospital and, when a patient presents stroke symptoms, the patient can be immediately scanned in the emergency room so as to determine if the patient is experiencing a stroke and, if so, to determine the nature of the stroke (i.e., hemorrhagic or ischemic). This may be done quickly and easily by moving the CT machine across the emergency room to the patient's gurney using the casters of gross movement mechanism 55 and then, while the patient remains on their gurney, scanning the patient by precision-advancing the CT machine relative to the patient using the centipede belt drives of fine movement mechanism 60, so that the scanning zone of the CT machine is moved relative to the patient. Thus, with the new CT machine 5, the patient can be scanned in the emergency room while remaining on their gurney, without ever having to be moved from the emergency room to the radiology department and then back again, thereby eliminating the traditional scanning delays associated with conventional CT scanners and thus facilitating proper stroke treatment.

X-Ray Tube Assembly 25

As noted above, it is desirable for novel CT machine 5 to be small, mobile and inexpensive in order to enhance its use in stroke applications. To that end, CT machine 5 includes a novel X-ray tube assembly 25 which addresses these goals. More specifically, X-ray tube assembly 25 is engineered so as to be relatively compact, lightweight and inexpensive.

Figure 4:
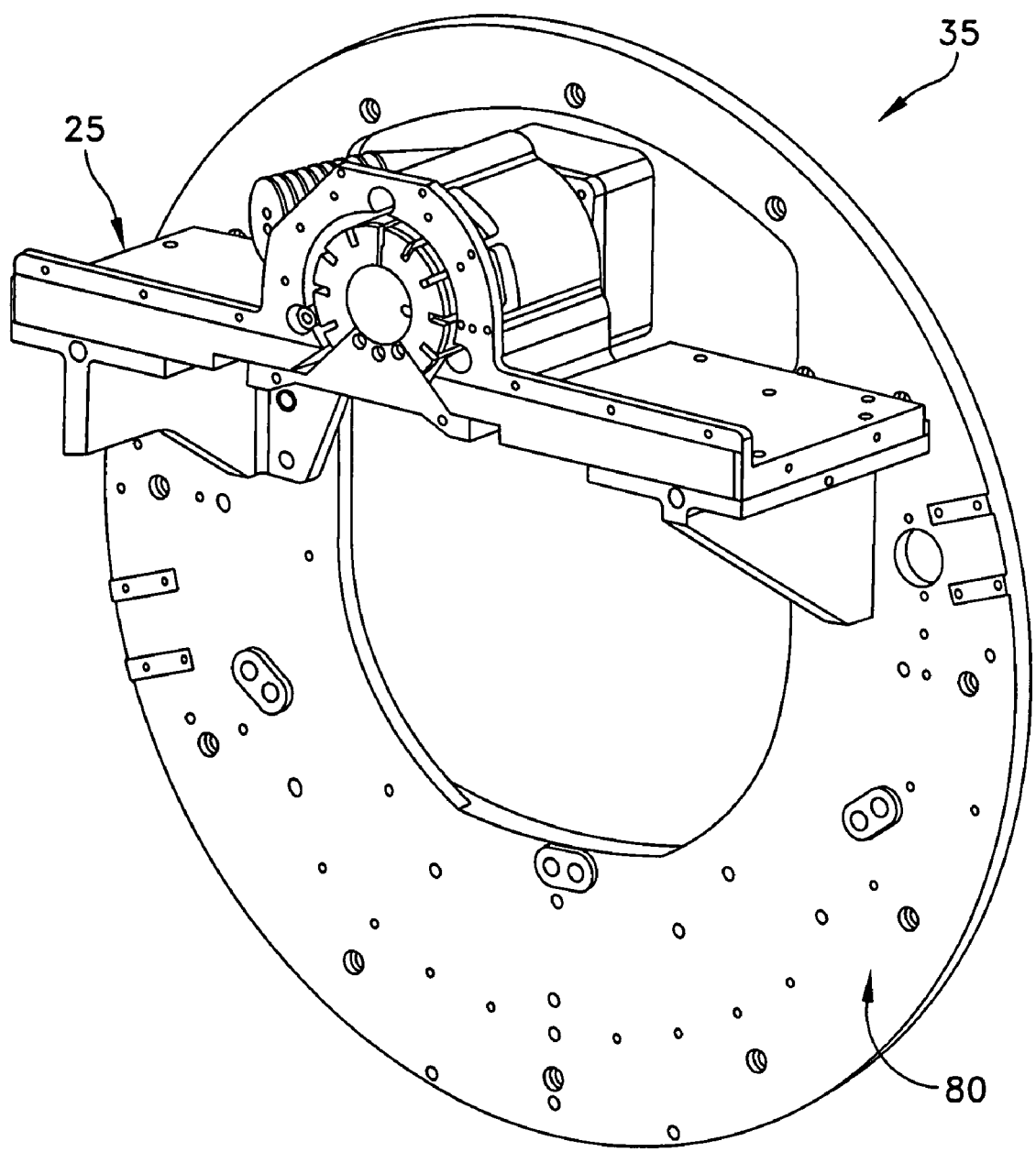
FIGS. 4 and 5 are schematic views showing a novel X-ray tube assembly and the rotating drum assembly of the CT machine shown in FIGS. 1-3.
Figure 5:
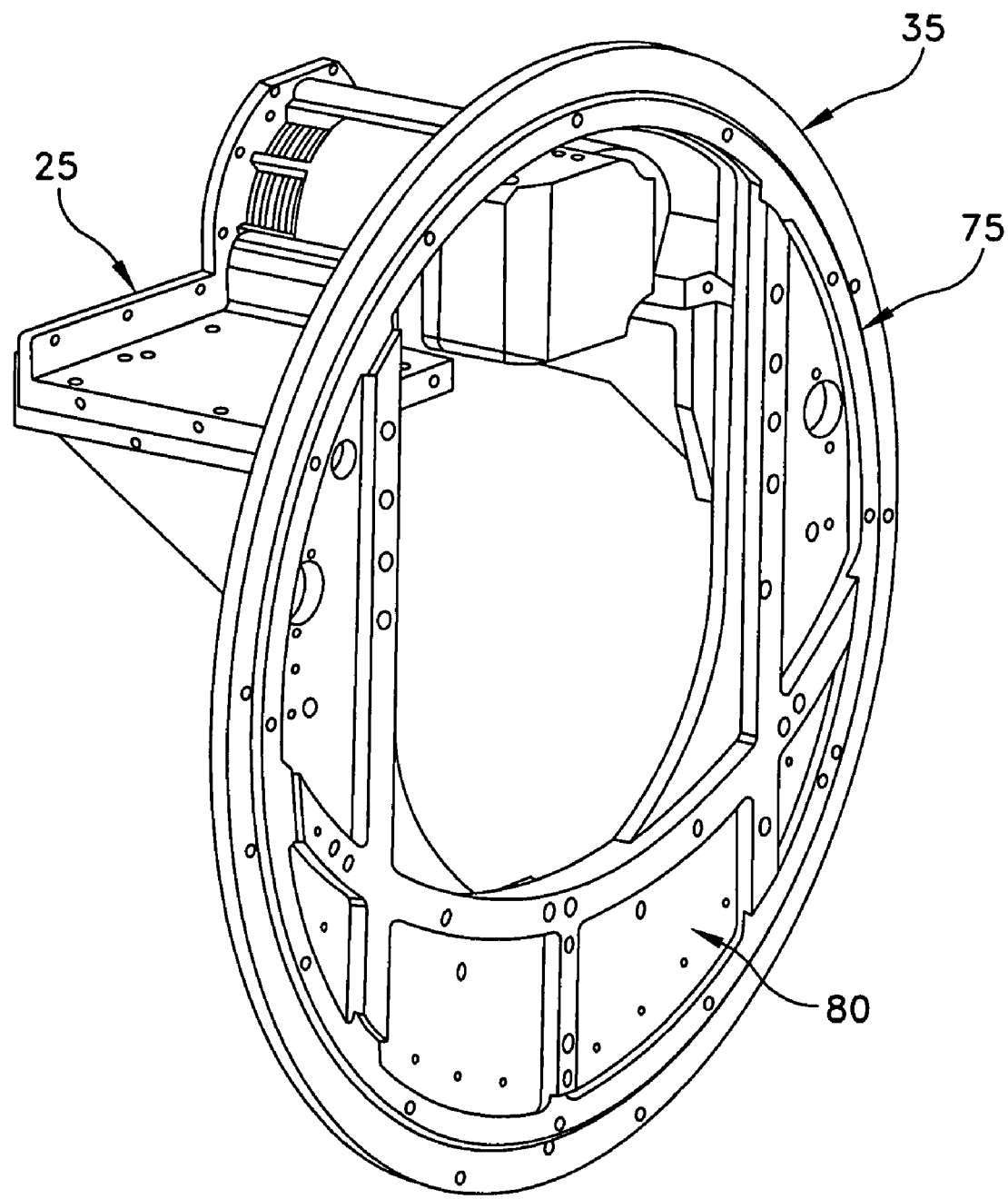
Figure 6:
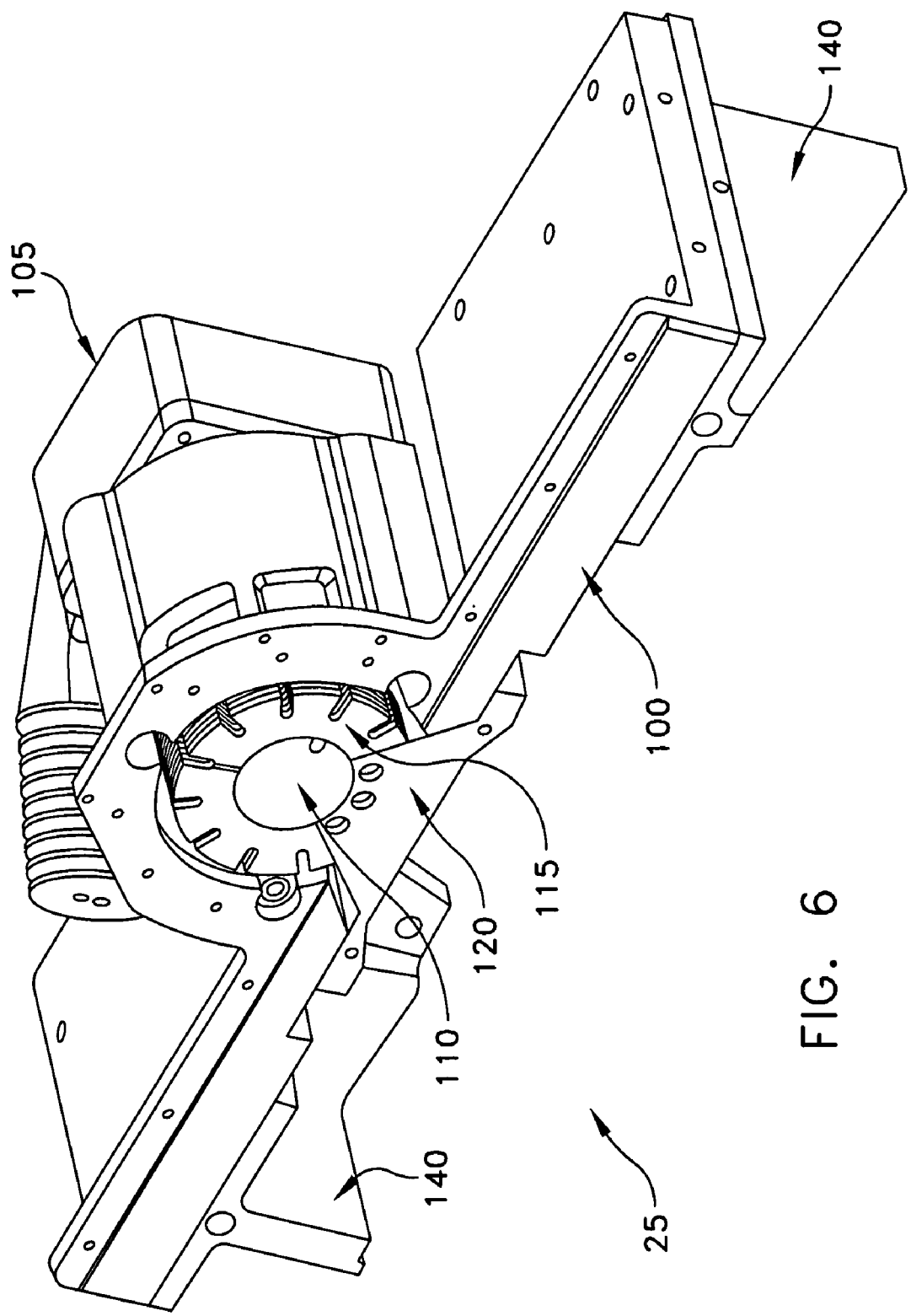
FIGS. 6-8 are schematic views of the novel X-ray tube assembly shown in FIG. 4.
Figure 7:
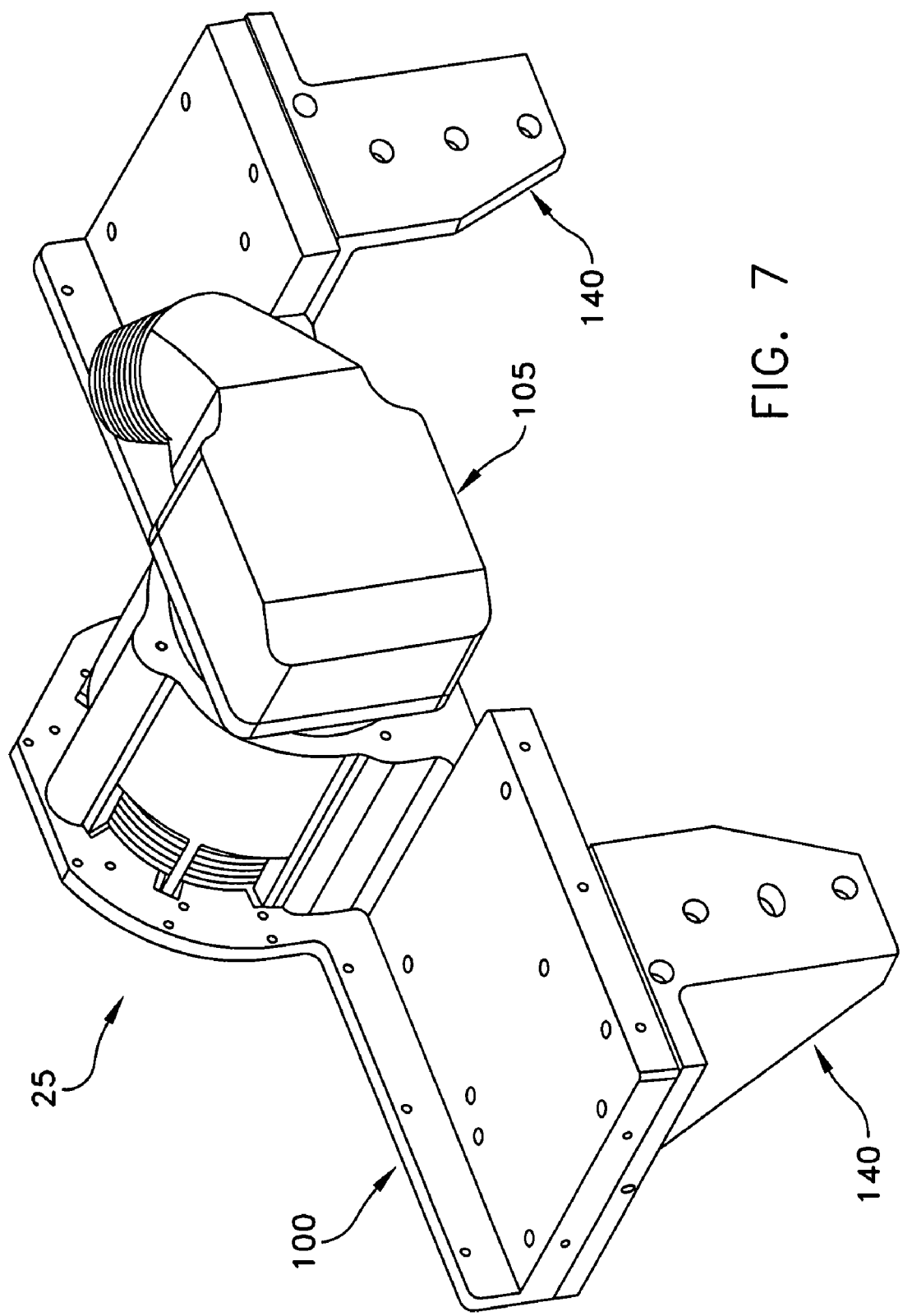
Figure 8:
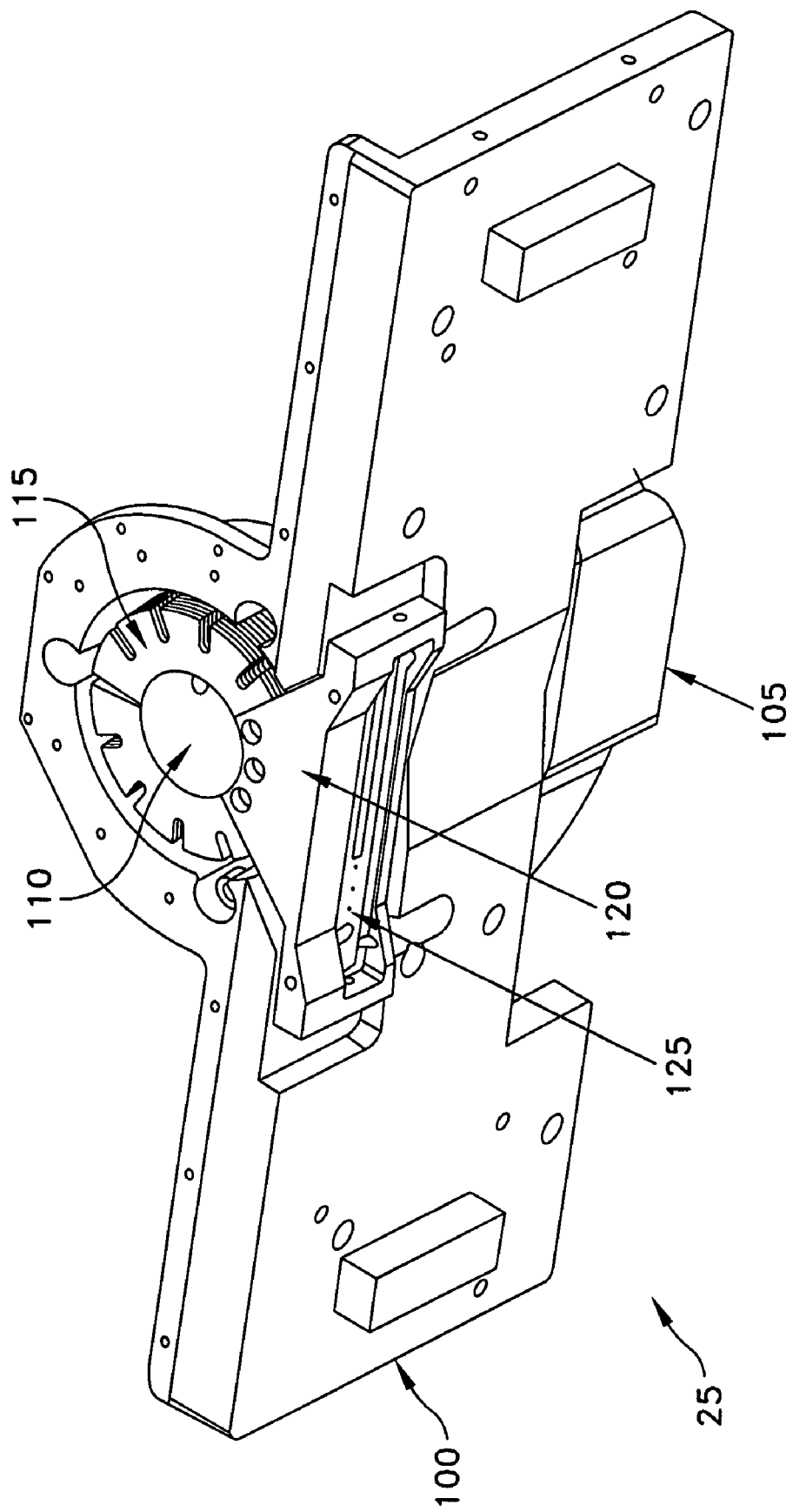
Figure 9:
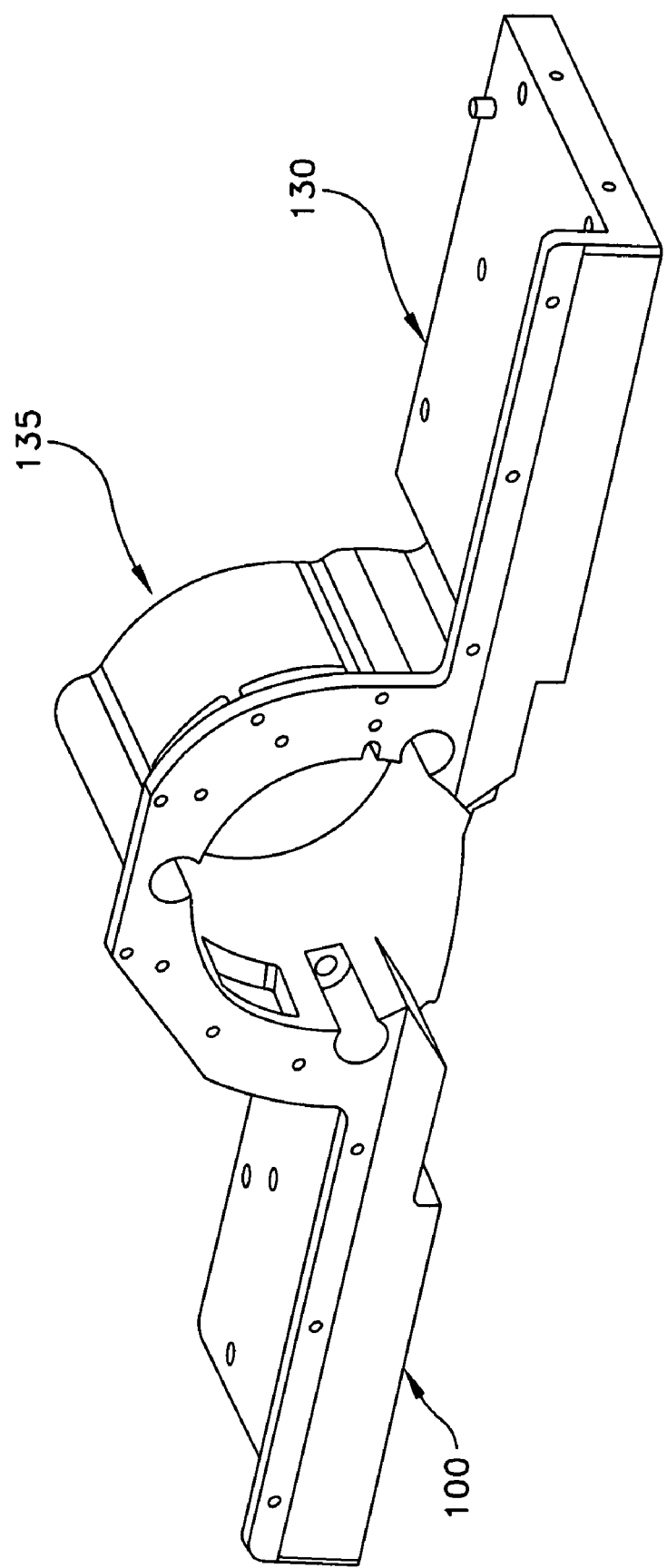
FIGS. 9 and 10 are schematic views showing the mount of the X-ray tube assembly shown in FIG. 4.
Figure 10:
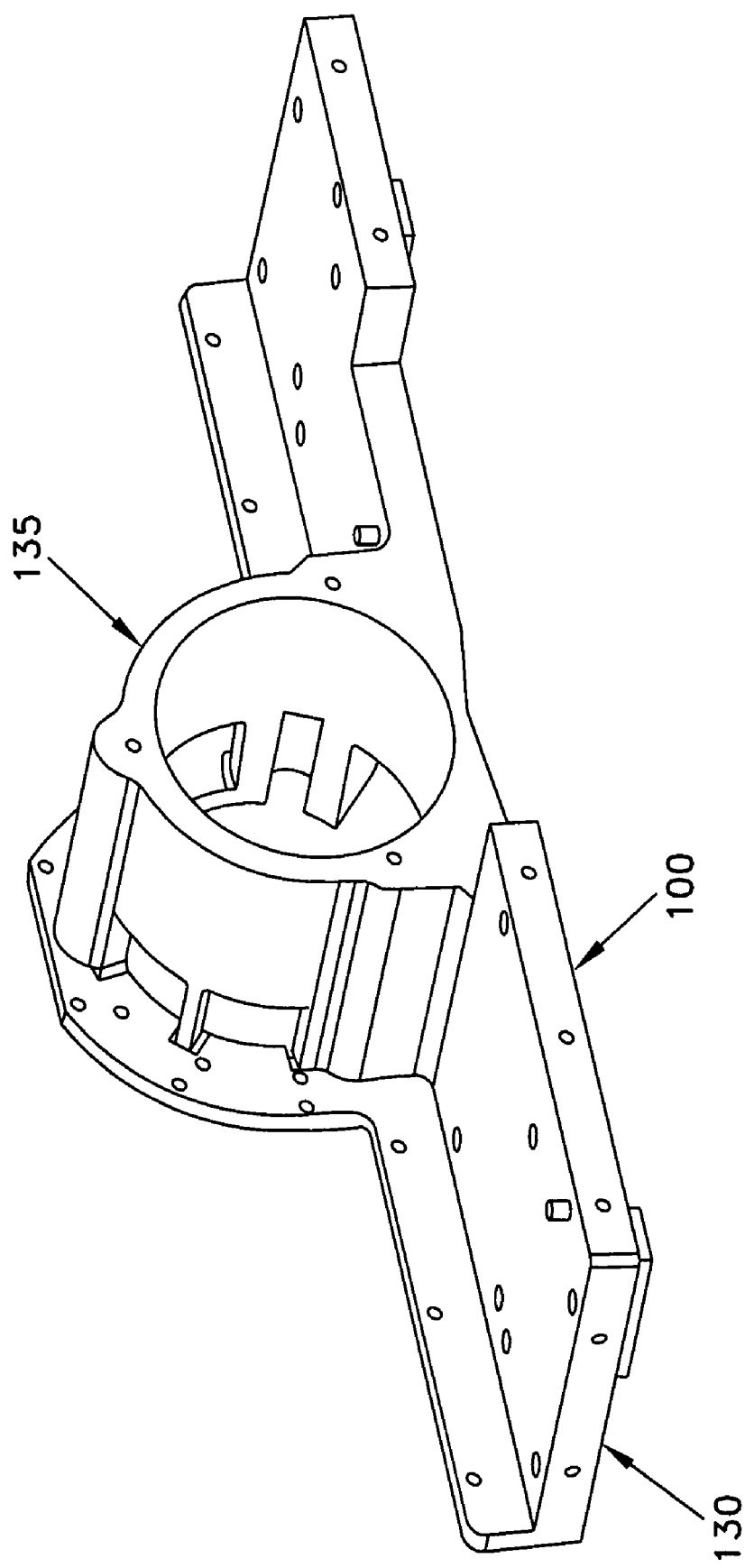
Figure 11:
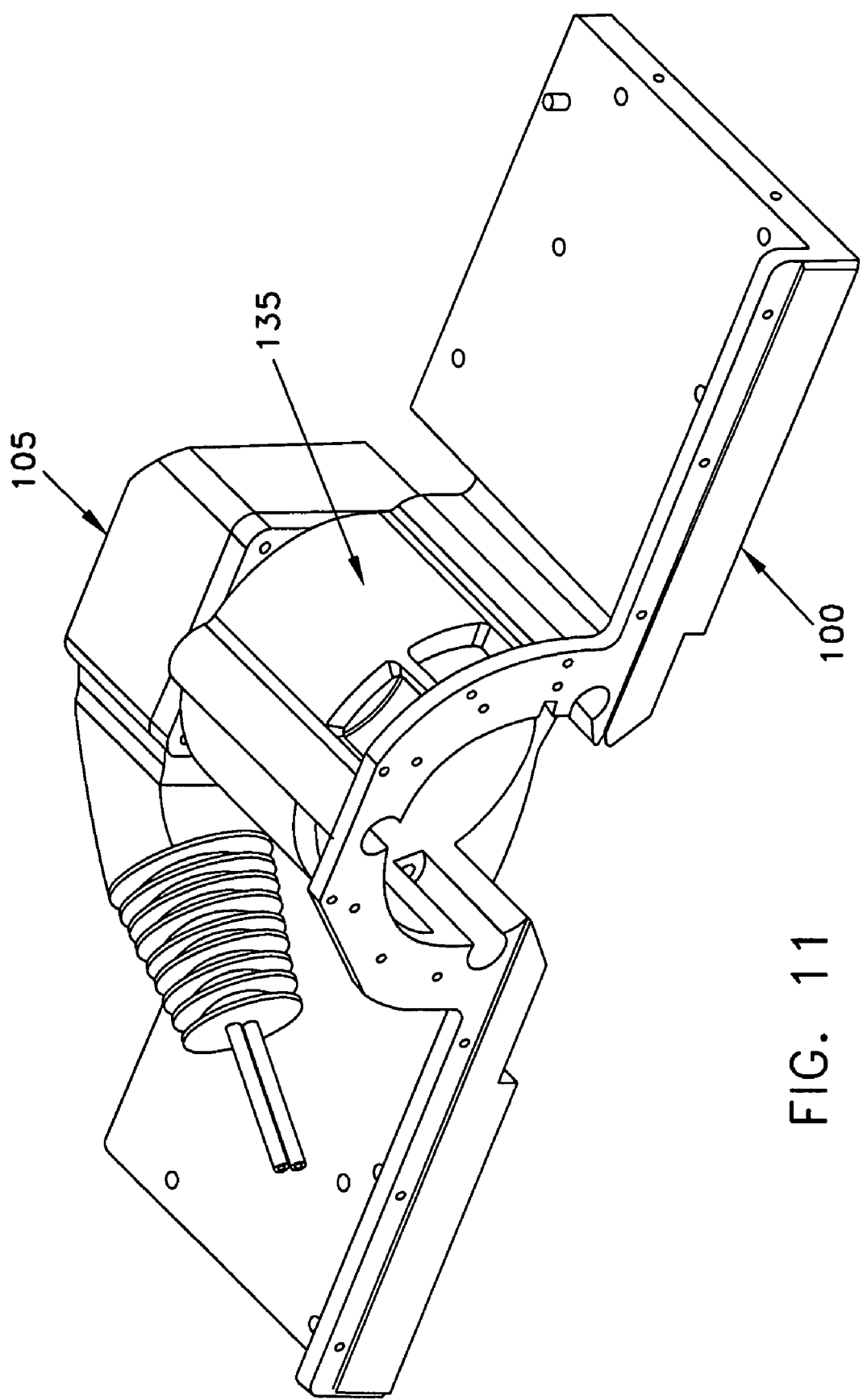
FIGS. 11-13 are schematic views showing the mount and the power connector of the X-ray tube assembly shown in FIG. 4.
Figure 12:
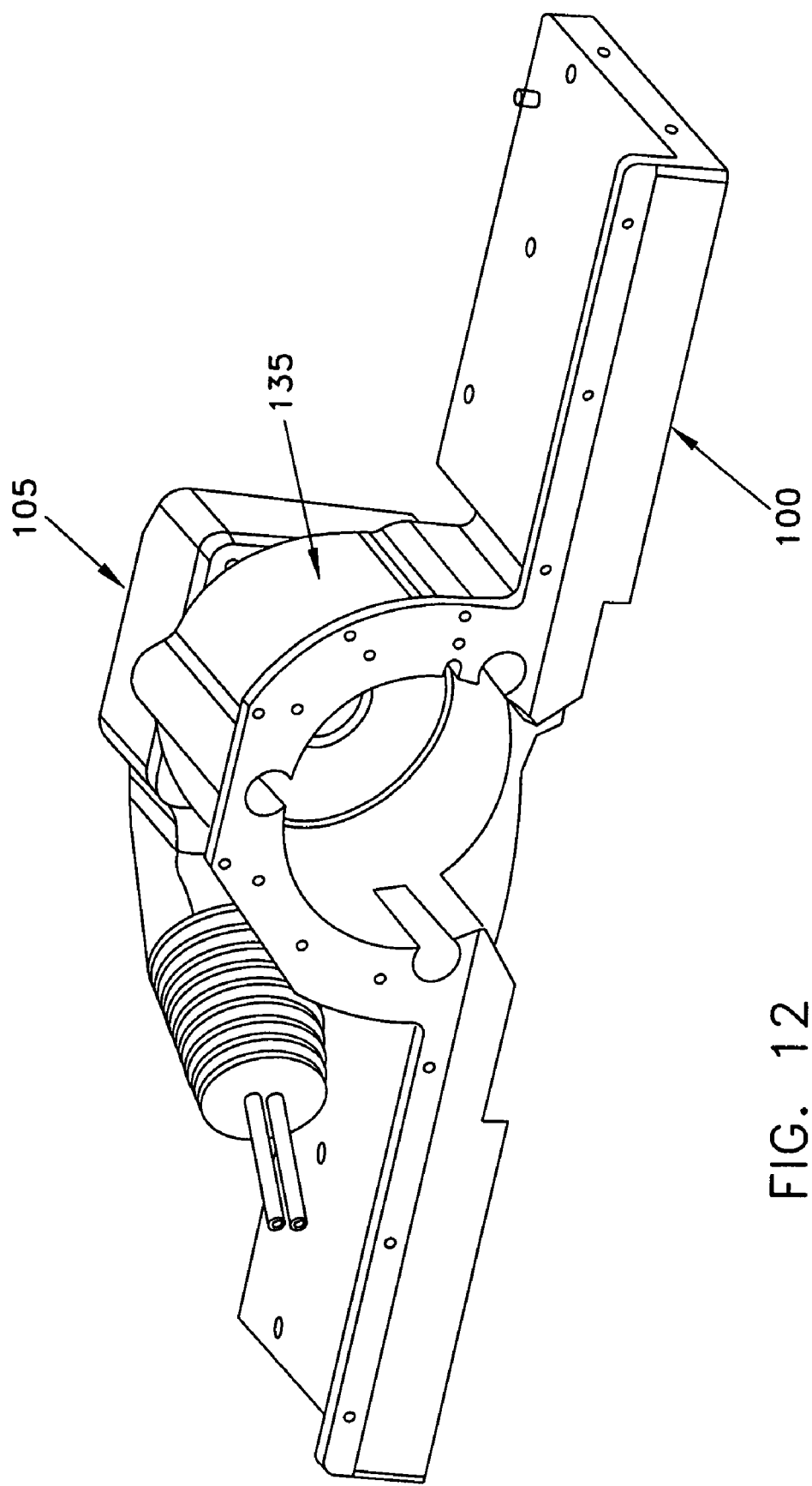
Figure 13:
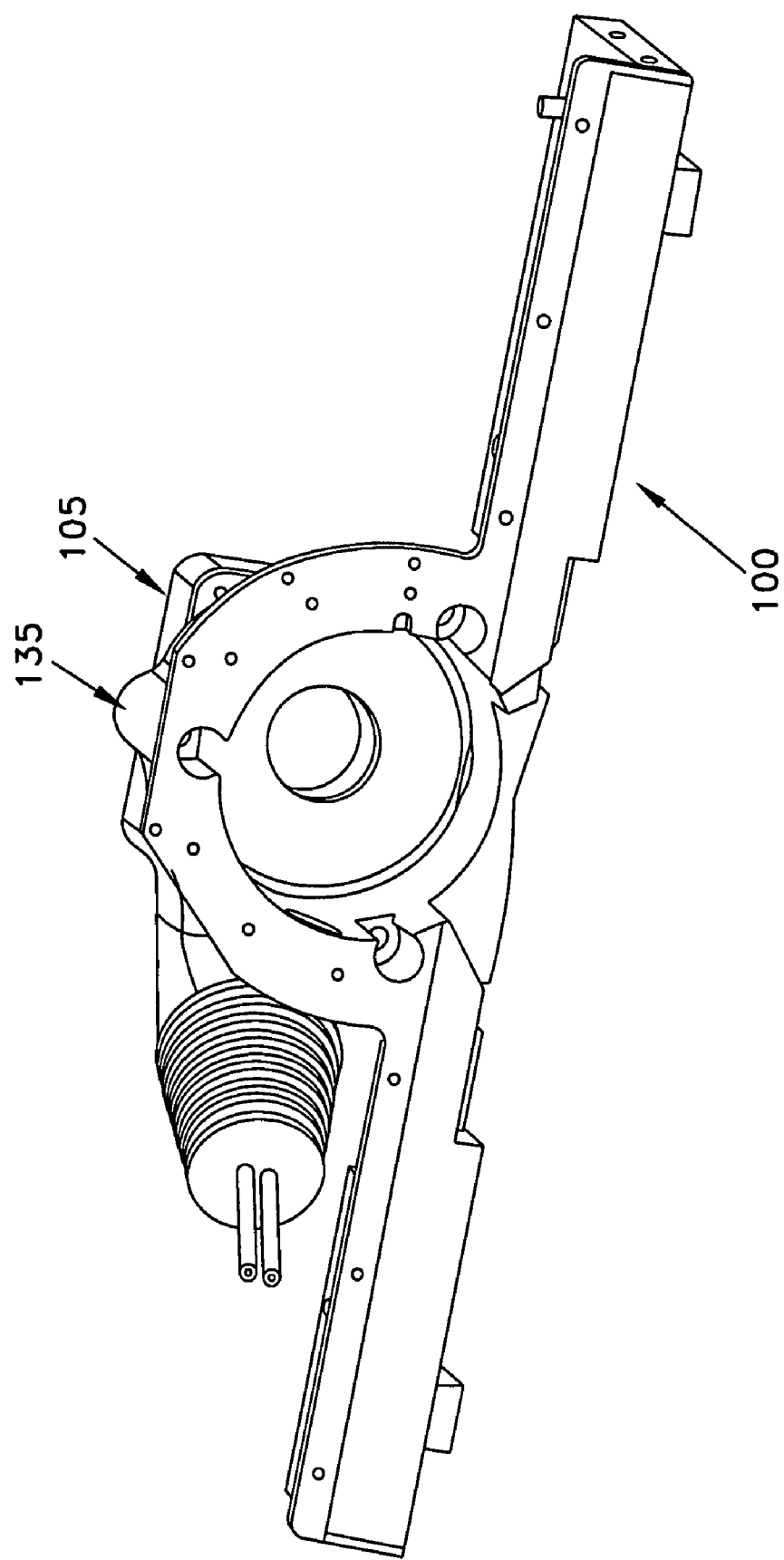

Looking now at FIGS. 4 and 5, there is shown the novel X-ray tube assembly 25 and rotating drum assembly 35. Rotating drum assembly 35 comprises an annular drum 75 (FIG. 5). A face plate 80 (FIGS. 4 and 5) is secured to the front side of annular drum 75, so that face plate 80 rotates in conjunction with annular drum 75. X-ray tube assembly 25 is mounted to face plate 80 so that the X-ray tube assembly 25 also rotates in conjunction with the drum.

Looking next at FIGS. 4-8, X-ray tube assembly 25 generally comprises a mount 100 for supporting the various components of X-ray tube assembly 25 and securing those components to face plate 80; a power connector 105 for delivering power from a power source to X-ray tube assembly 25; an X-ray tube 110 for emitting X-rays; a heat sink 115 for drawing heat away from X-ray tube 110; a collimator support 120; and a collimator 125 for collimating the X-rays emitted by X-ray tube 110 and "focusing" those X-rays on X-ray detector 30 (FIG. 3). The various components of the novel X-ray tube assembly 25 are designed to interconnect with one another so as to collectively form a relatively compact, lightweight and inexpensive "monoblock" assembly as shown in FIGS. 4-8.

More particularly, and looking now at FIGS. 6-8, 9 and 10, mount 100 generally comprises a frame 130 which includes a canister 135 for receiving other components, as will hereinafter be discussed, and a pair of brackets 140 (FIGS. 6 and 7) for securing frame 130 to face plate 80. Additionally, and looking now at FIGS. 6-8 and 11-13, power connector 105 is attached to mount 100 so as to supply power contacts to, and close off, the rear end of canister 135.

Figure 14:
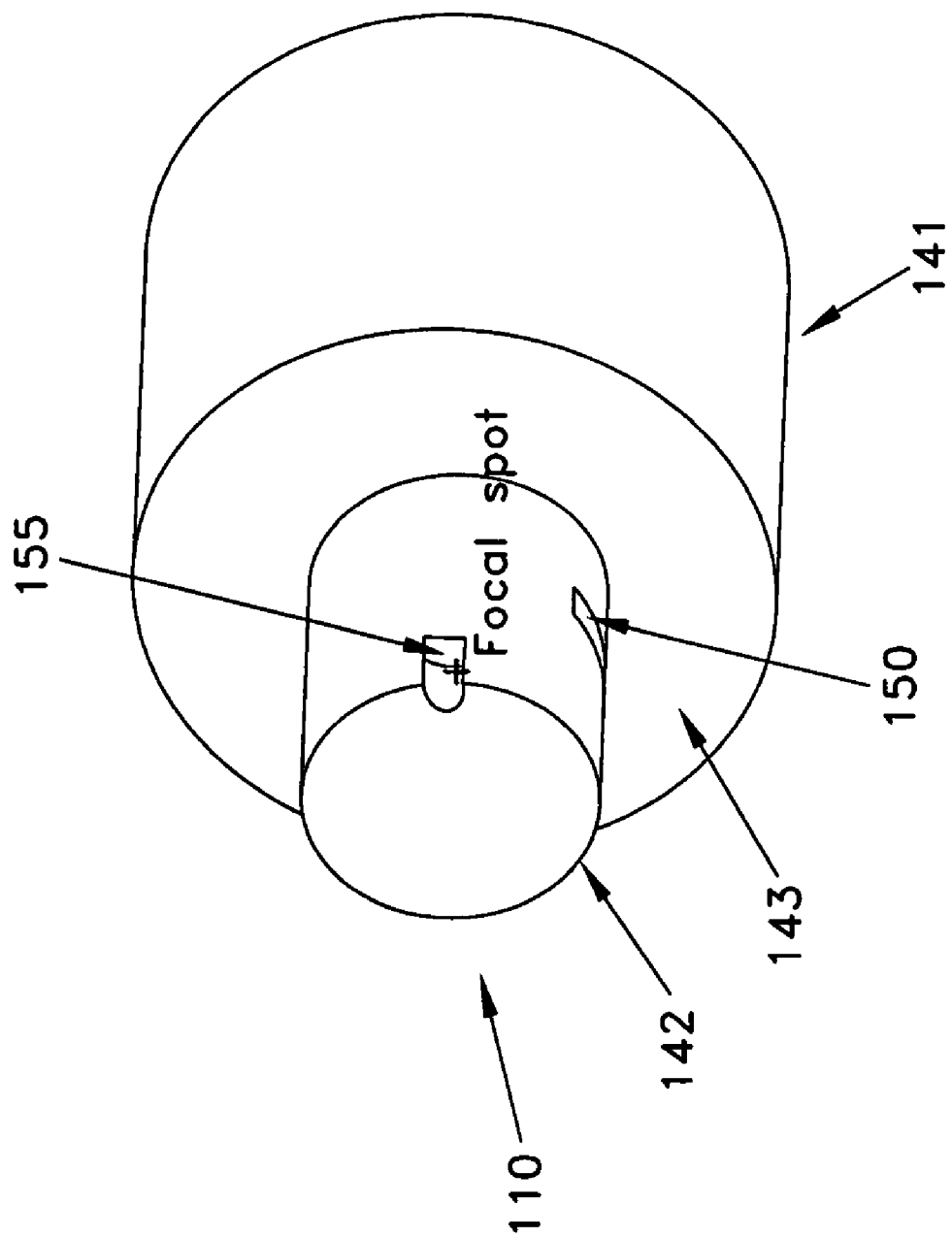
FIGS. 14 and 15 are schematic views showing the X-ray tube of the X-ray tube assembly shown in FIG. 4.
Figure 15:
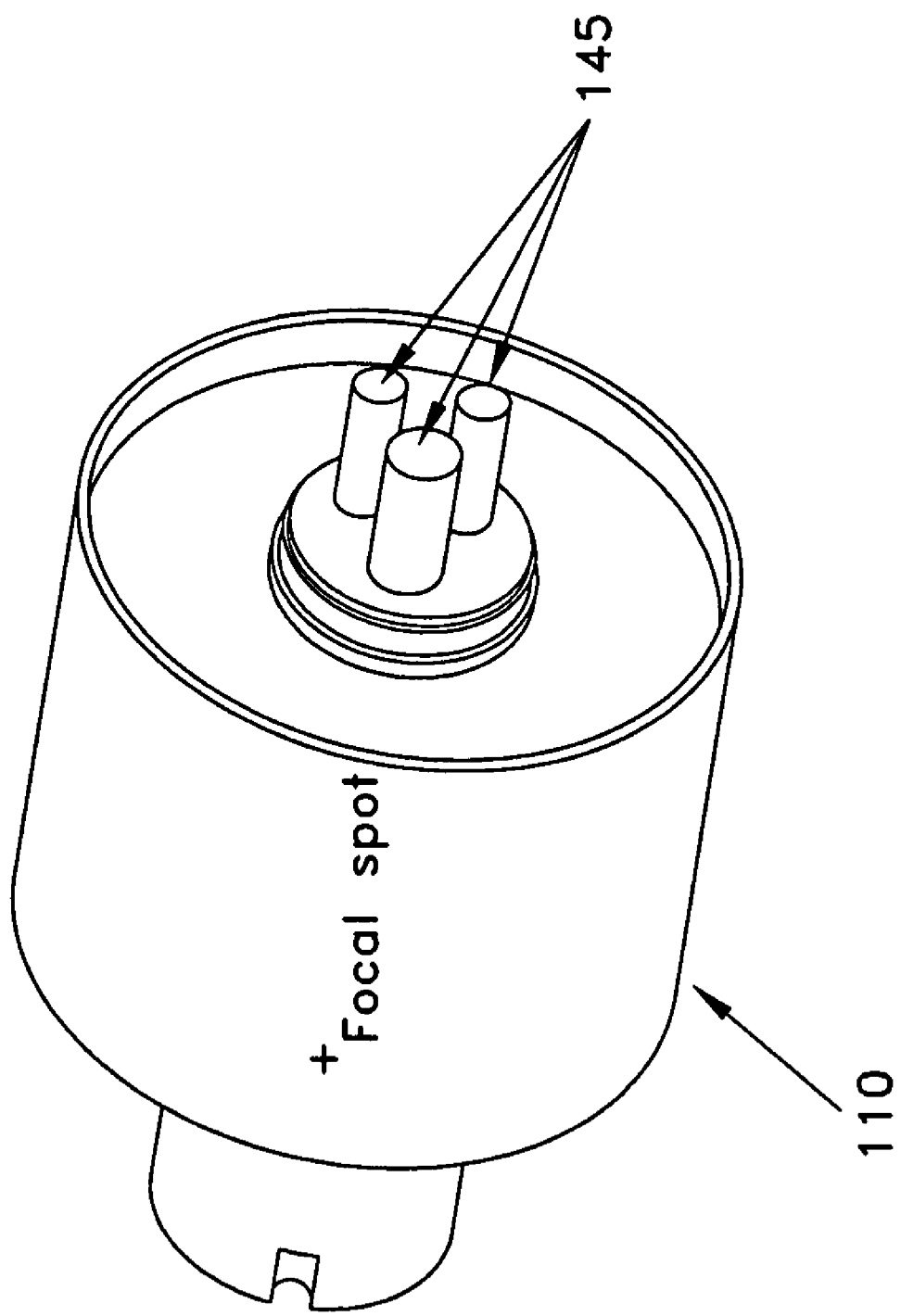

X-ray tube 110 is shown in FIGS. 14 and 15. X-ray tube 110 is preferably of the sort well known in the art (e.g., it may be a RAD-12™ Rotating Anode X-ray Tube of the sort manufactured by Varian Medical Systems of Palo Alto, Calif.), and is generally characterized by a rear cylindrical portion 141, a front cylindrical portion 142, an annular face 143 formed at the intersection of rear cylindrical portion 141 and front cylindrical portion 142, rear electrical connectors 145 for delivering power to X-ray tube 110, an emitter opening 150 for emitting X-rays from the X-ray tube, and an alignment keyway 155 for use in appropriately aligning X-ray tube 110 in the X-ray tube assembly 25, as will hereinafter be discussed. While not shown in the drawings, it will be appreciated by those skilled in the art that the X-ray tube's anode is disposed in front cylindrical portion 142, adjacent to emitter opening 150.

Figure 16:
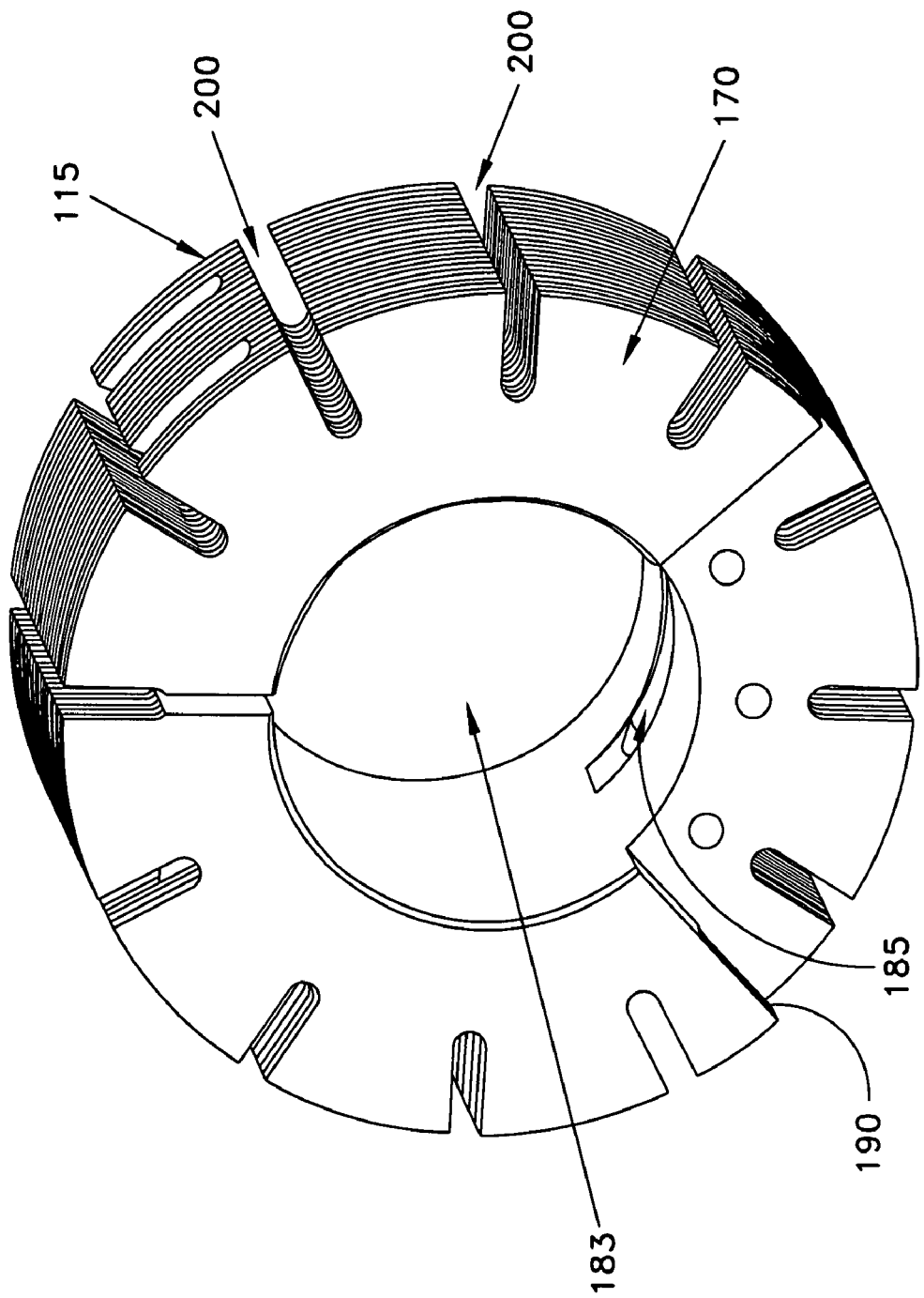
FIGS. 16 and 17 are schematic views showing various aspects of the heat sink of the X-ray tube assembly shown in FIG. 4.
Figure 17:
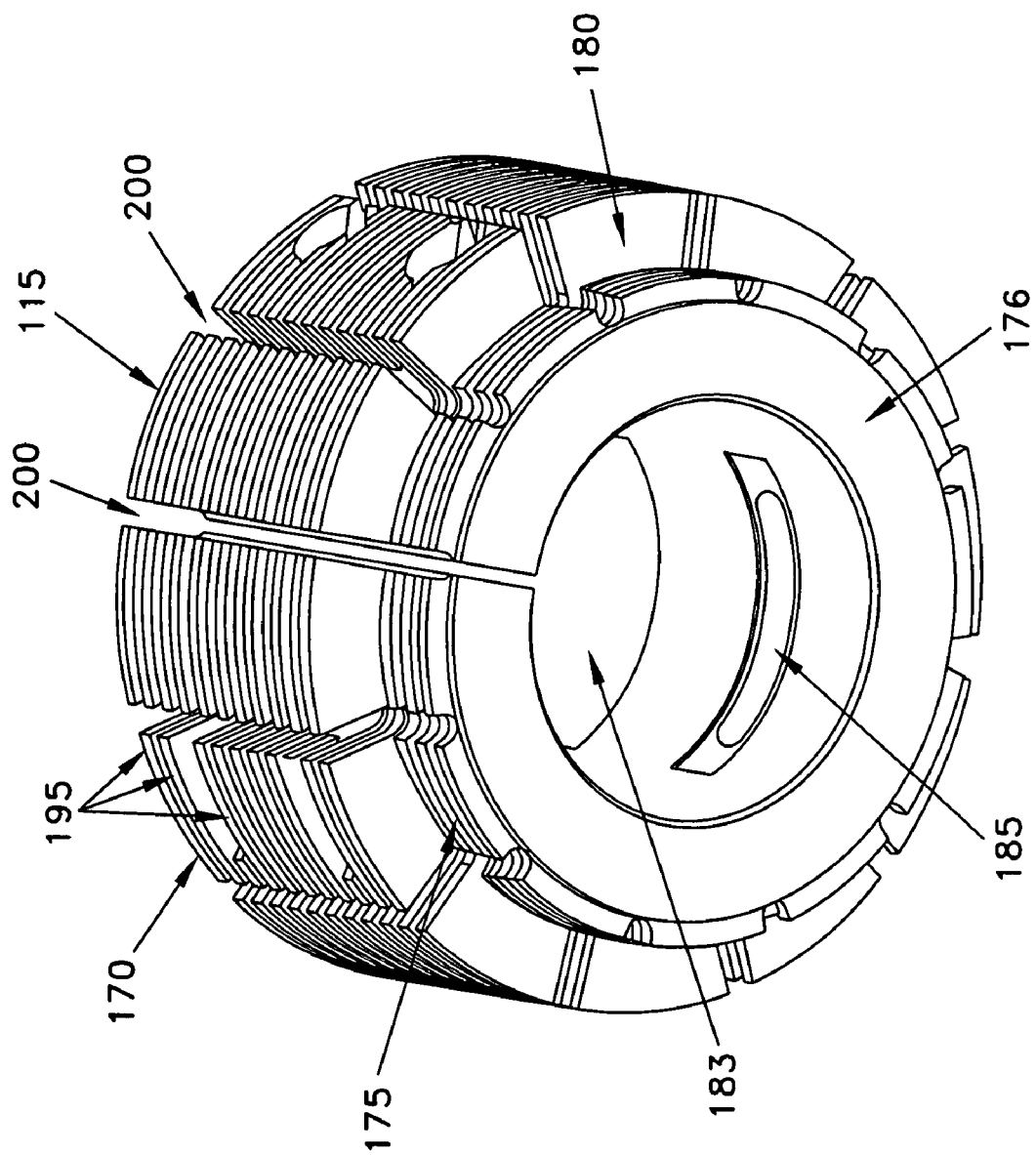

Looking next at FIGS. 16 and 17, heat sink 115 is characterized by a front cylindrical portion 170, a rear cylindrical portion 175 terminating in an end surface 176, an annular face 180 formed at the intersection of front cylindrical portion 170 and rear cylindrical portion 175, an axial opening 183 extending along the length of heat sink 115, a window 185 for passing X-rays through heat sink 115, and a front recess 190 (FIG. 16) for receiving a portion of collimator support 120, whereby to connect collimator 125 to heat sink 115, as will hereinafter be discussed. In order to increase the heat transfer capacity of heat sink 115, it is preferable to have multiple openings formed in the heat sink, whereby to increase its effective surface area. These multiple openings are preferably in the form of a plurality of circumferential slots 195, and a plurality of radial slots 200, formed in both front cylindrical portion 170 and rear cylindrical portion 175.

Figure 18:
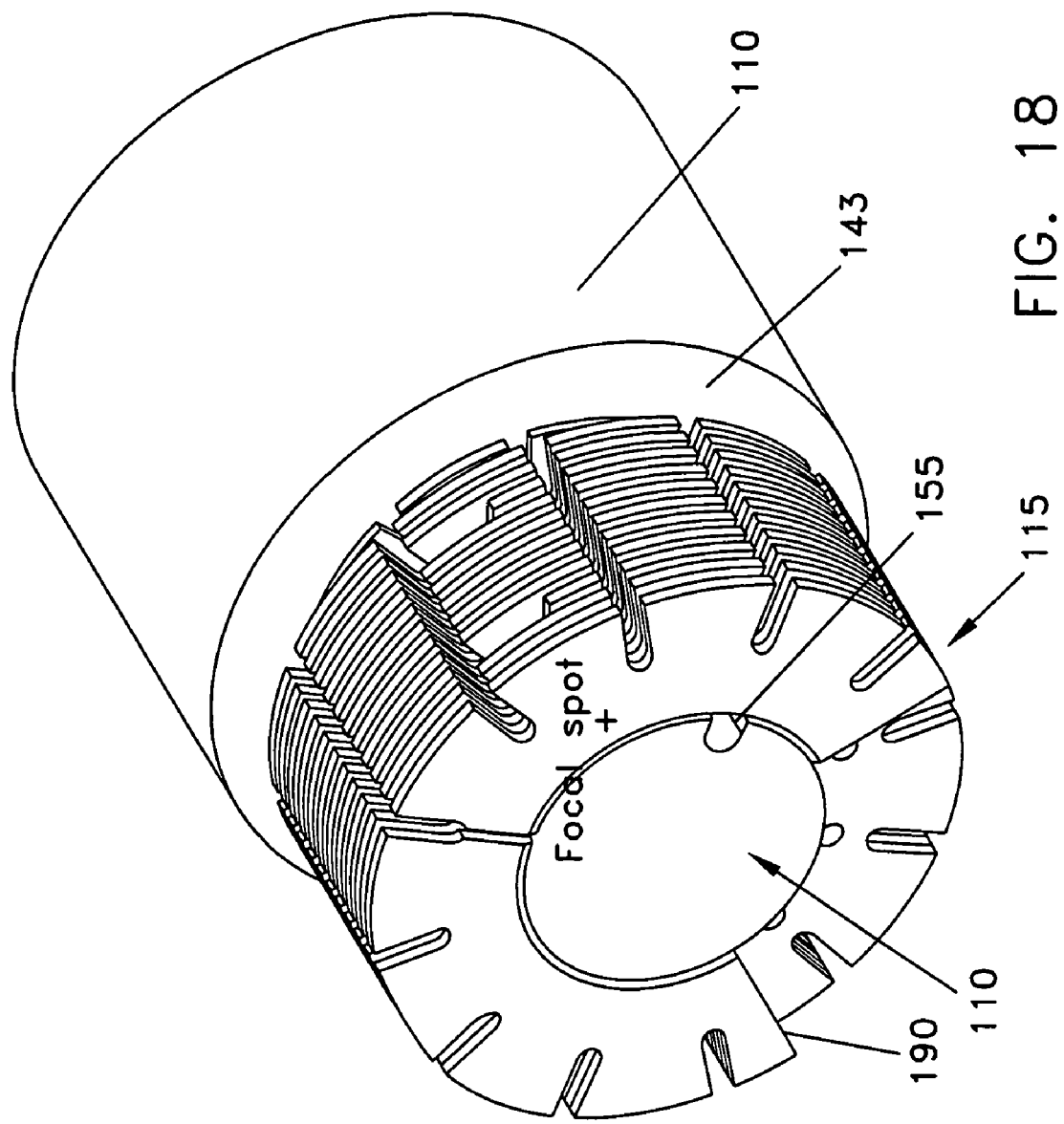
FIG. 18 is a schematic view showing the heat sink mounted to the X-ray tube.

As seen in FIG. 18, heat sink 115 is mounted onto X-ray tube 110 by seating heat sink 115 on the X-ray tube's front cylindrical portion 142, with the rear surface 176 (FIG. 17) of heat sink 115 engaging annular face 143 (FIG. 14) of the X-ray tube, and with window 185 (FIGS. 16 an 17) of heat sink 115 aligned with emitter opening 150 (FIG. 14) of X-ray tube 110. This arrangement positions the heat-conveying mass of heat sink 115 adjacent to the heat-producing anode of X-ray tube 110, and permits X-rays exiting emitter opening 150 to pass through the heat sink via window 185.

Figure 19:
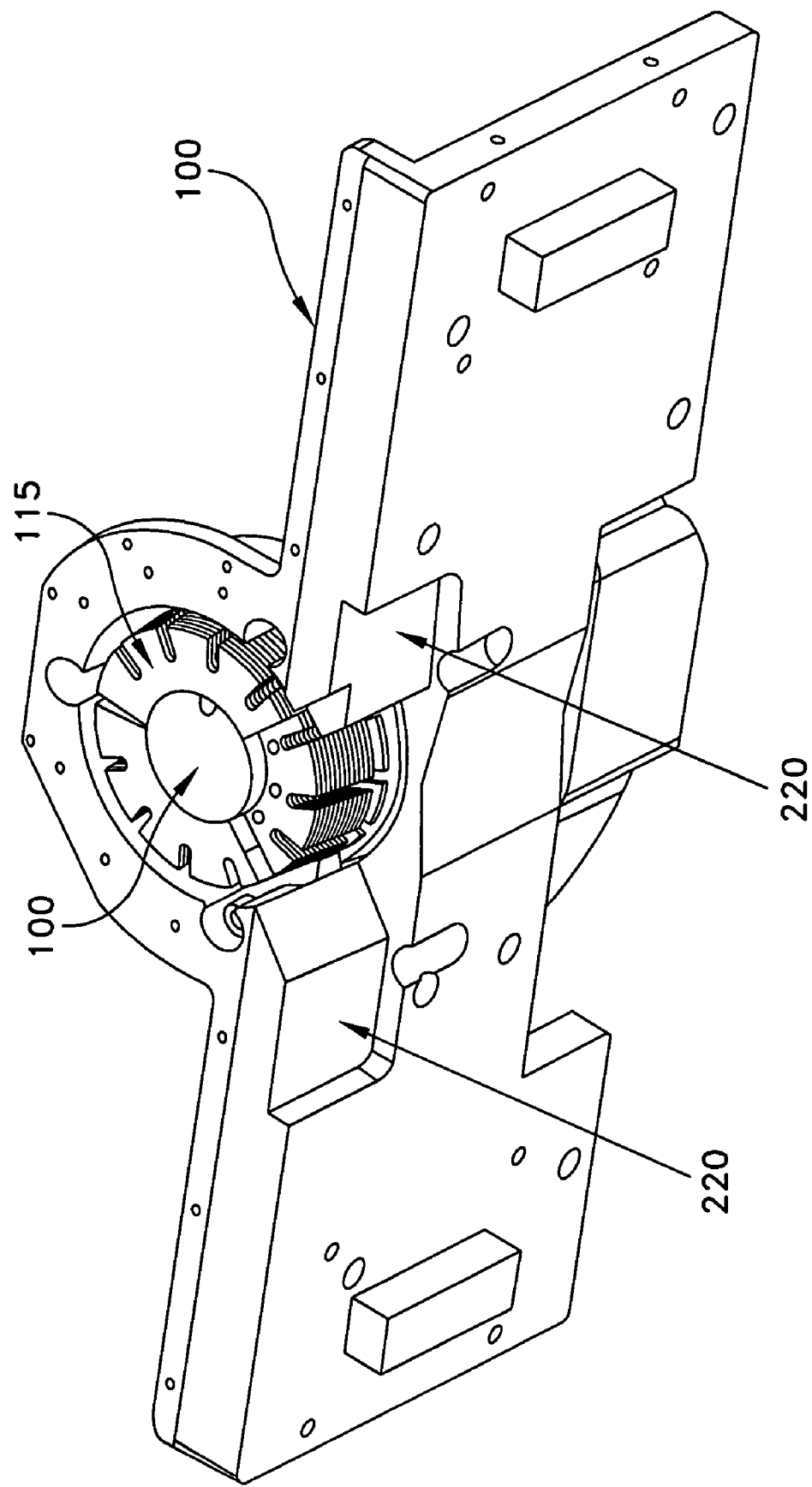
FIGS. 19-22 are schematic views showing the X-ray tube and heat sink secured to the mount and the power connector of the X-ray tube assembly shown in FIG. 4 (but with the heat sink rendered transparent in FIGS. 21 and 22 so as to reveal further aspects of the construction)
Figure 20:
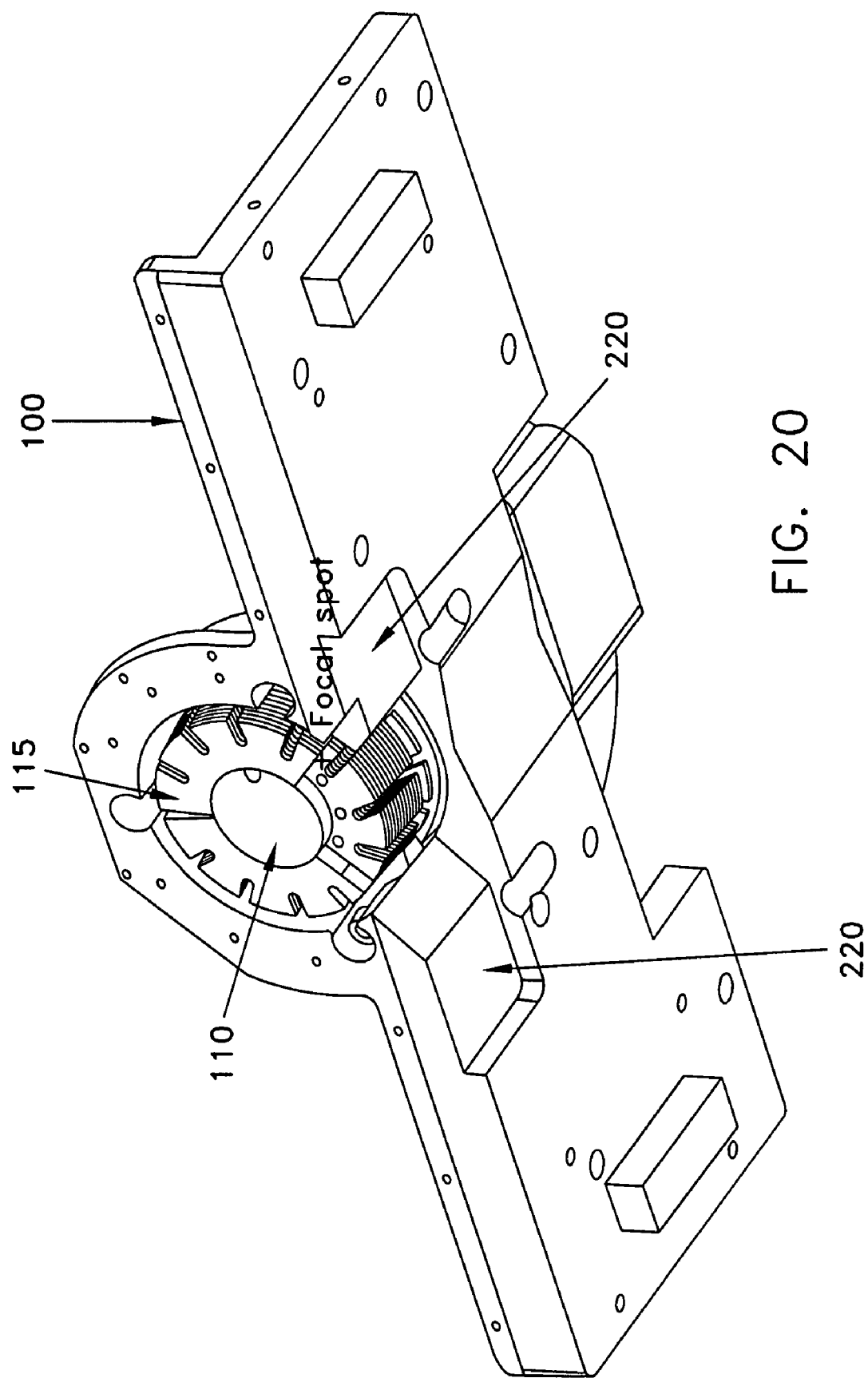
Figure 21:
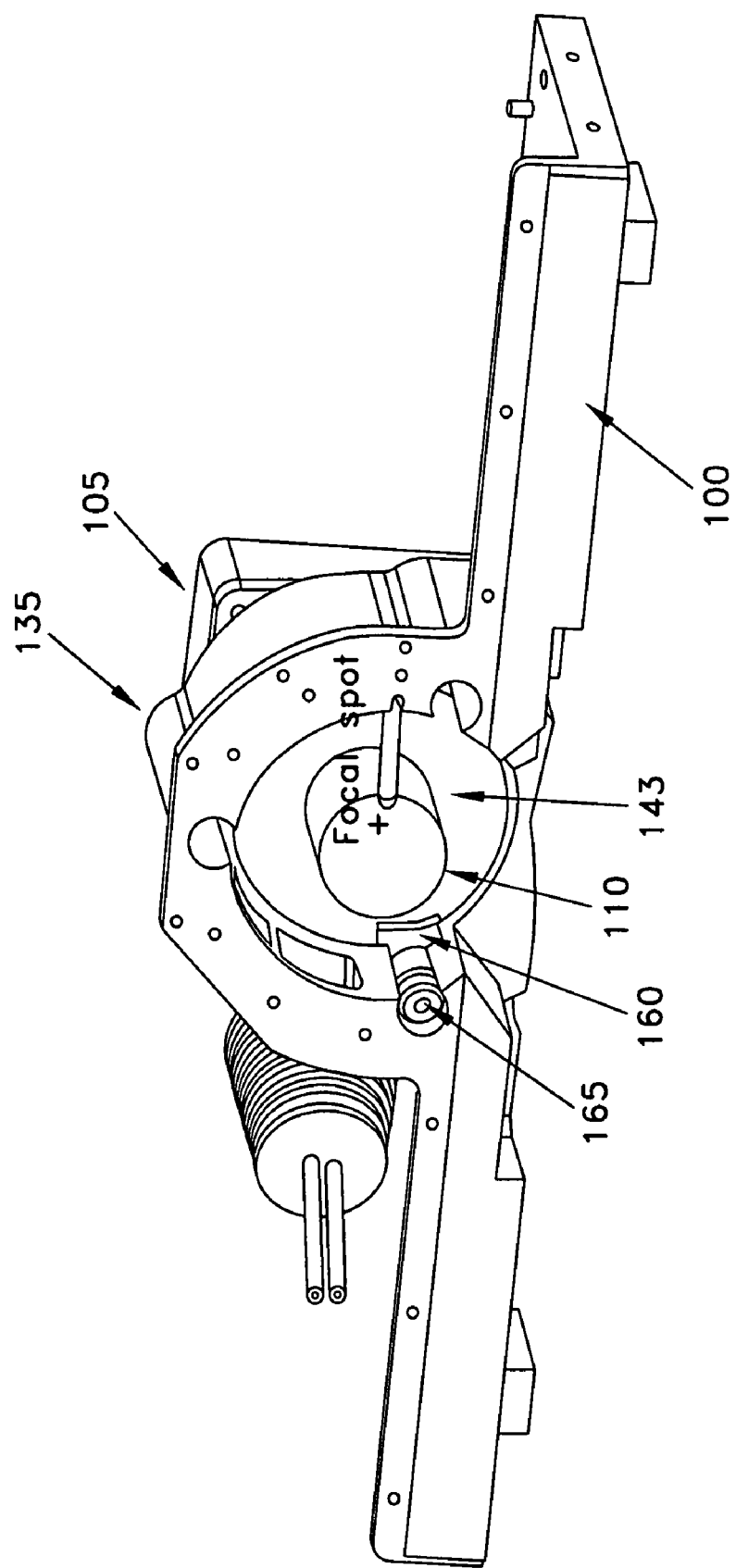
Figure 22:
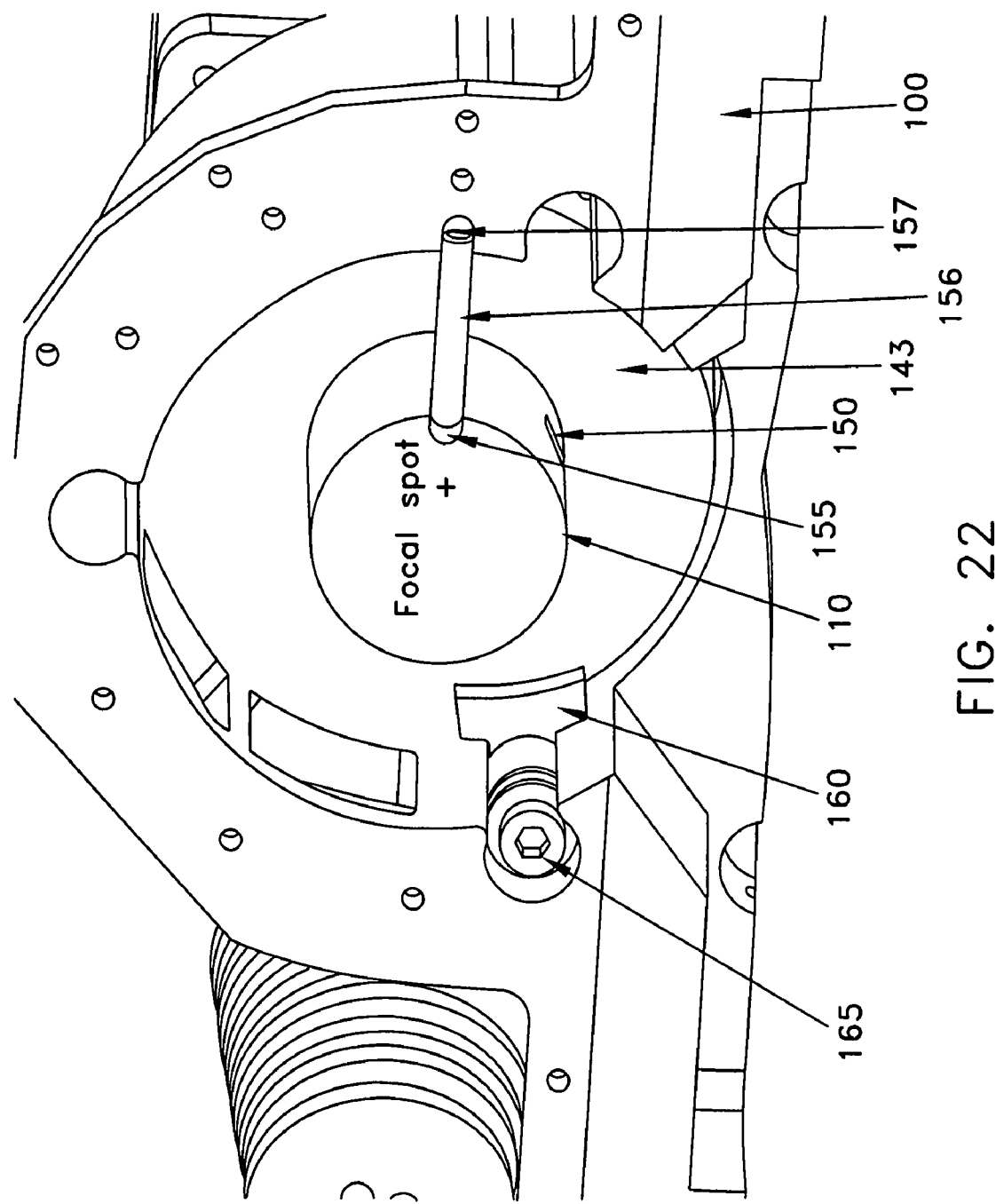
Figure 23:
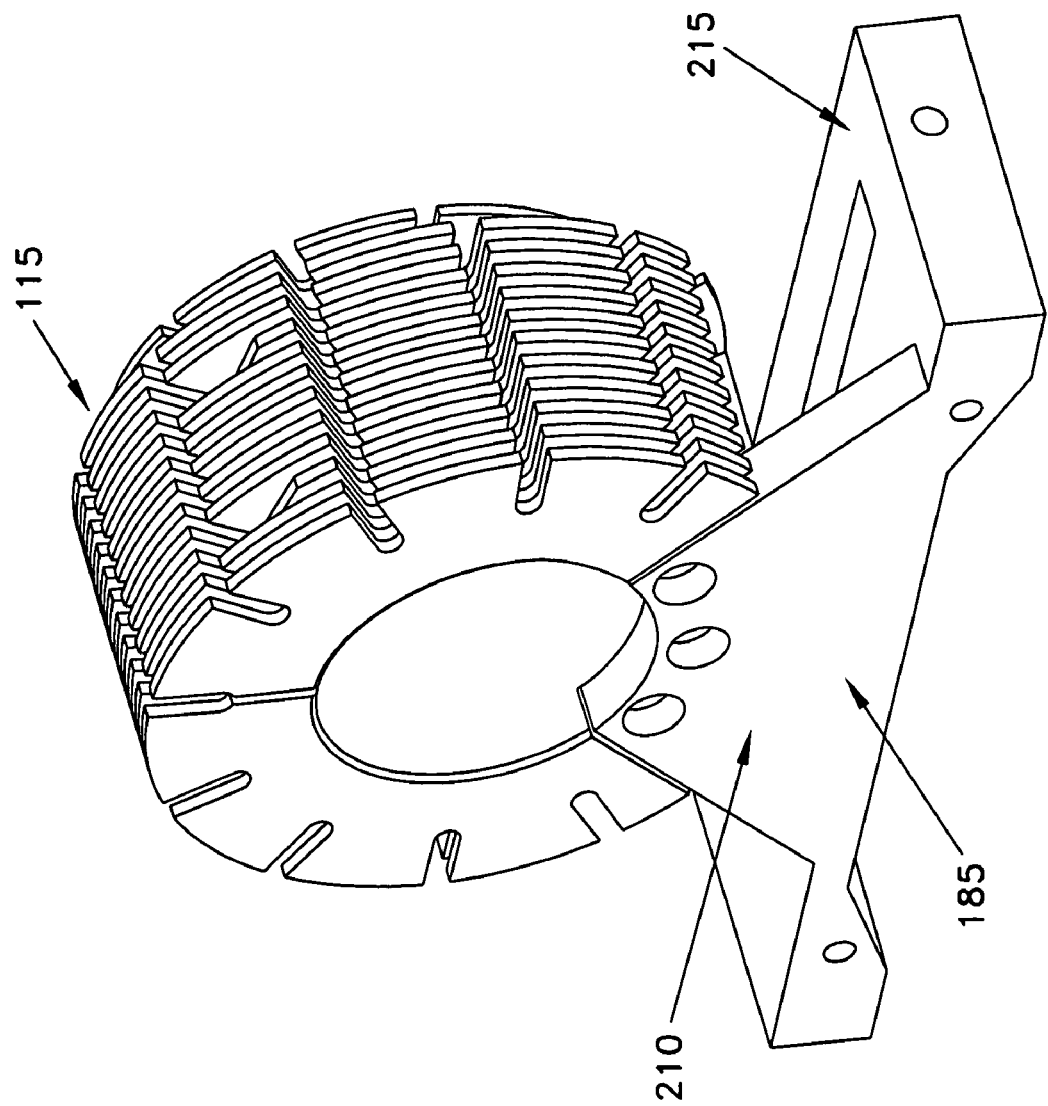
FIGS. 23-25 are schematic views showing various aspects of the collimator and the collimator support of the X-ray tube assembly shown in FIG. 4.
Figure 24:
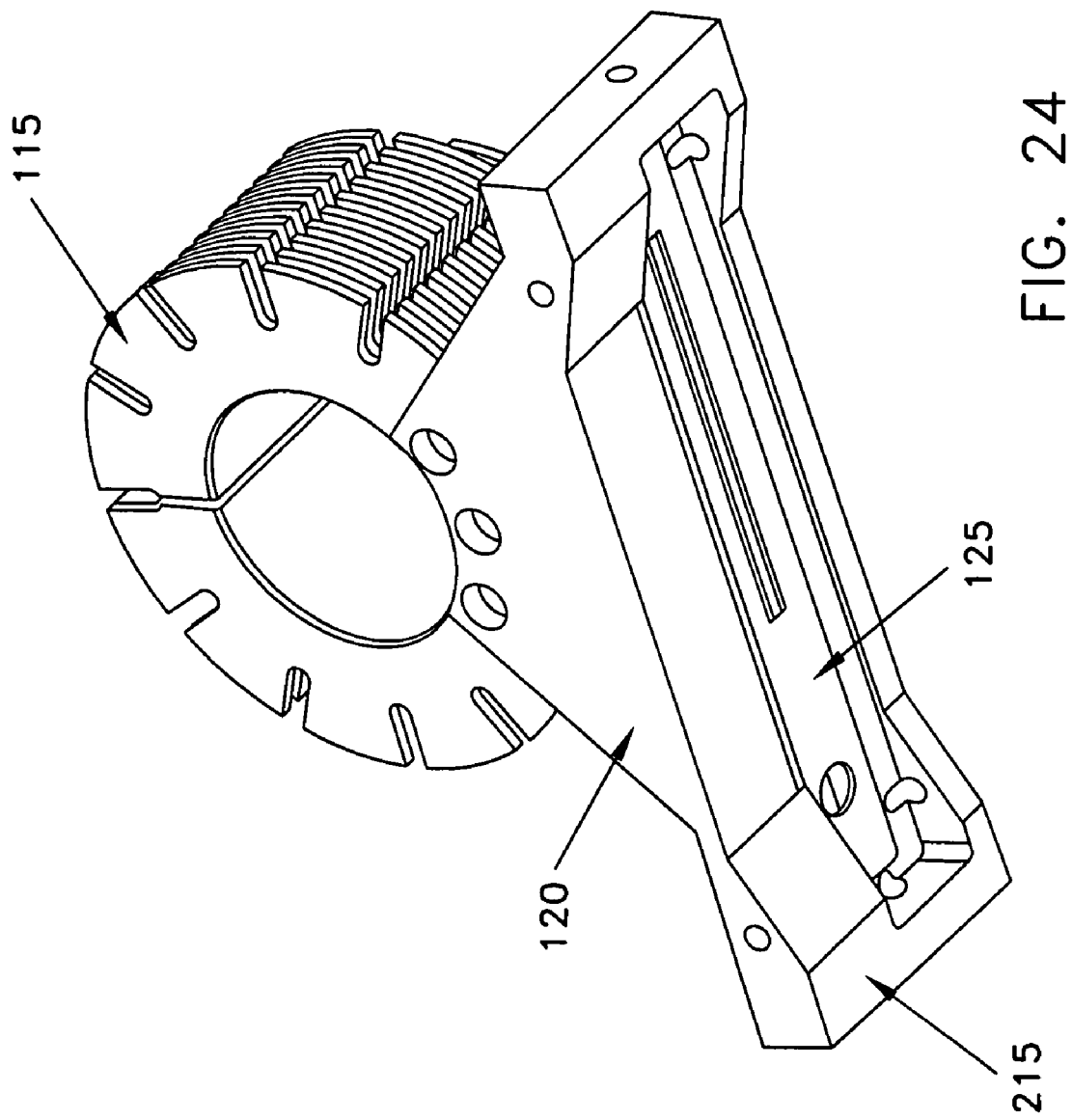
Figure 25:
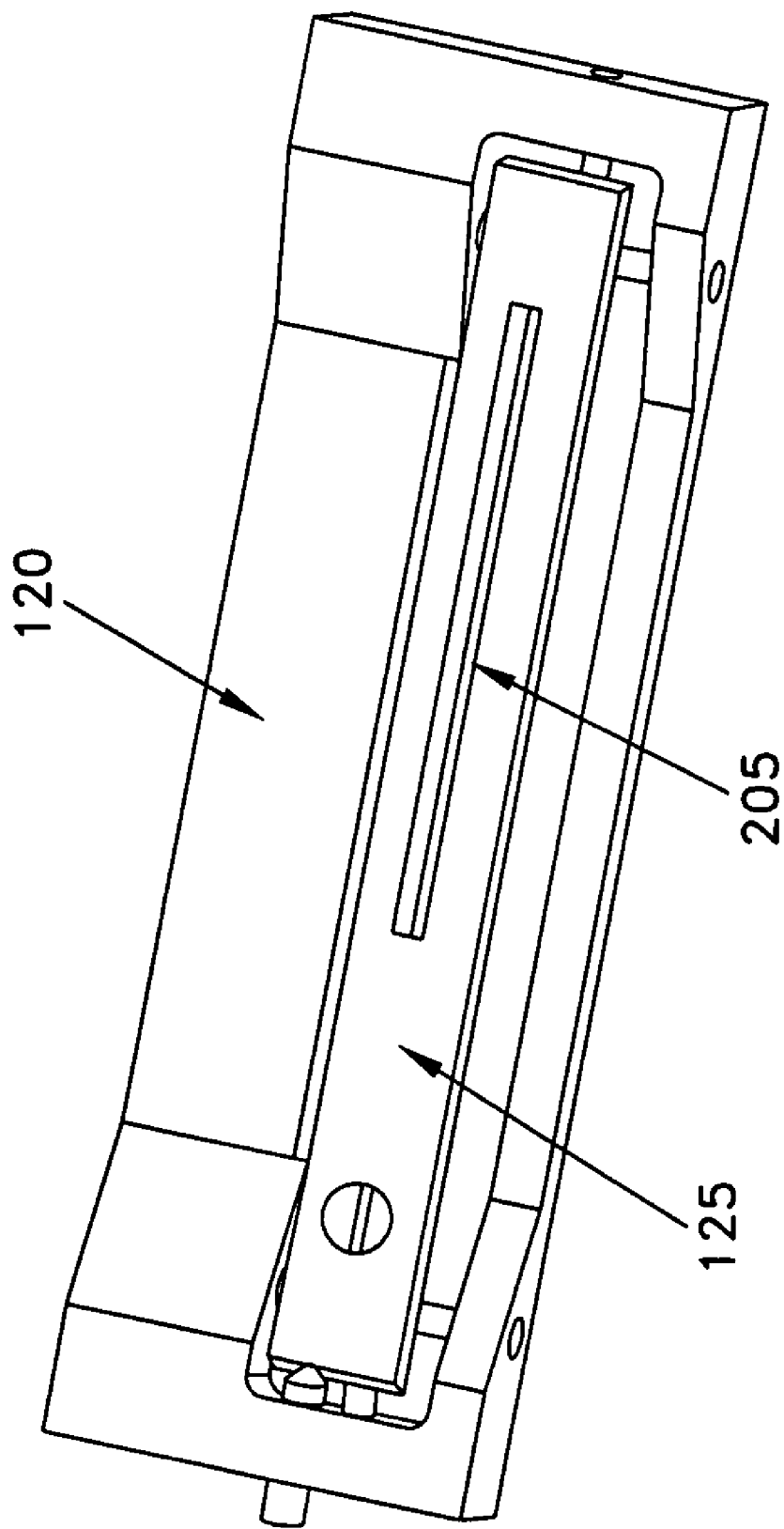

As seen in FIGS. 19 and 20, X-ray tube 110 and heat sink 115 are positioned, as a subassembly, in canister 135 so that the X-ray tube's electrical connectors 145 electrically connect to power connector 105, whereby to deliver electrical power to X-ray tube 110. As seen in FIGS. 21 and 22, which show the assembly with the heat sink rendered transparent so as to show additional construction details, an alignment pin 156 (FIG. 22) is used to align the alignment keyway 155 in X-ray tube 110 with a corresponding alignment keyway 157 formed in canister 135, whereby to ensure proper orientation of the X-ray tube relative to mount 100. A plurality of clamps 160 (FIGS. 21 and 22), secured by bolts 165, engage annular face 143 of the X-ray tube so as to secure X-ray tube 110 in position within canister 135. Preferably Belleville washers (or other spring washers) are provided to accommodate any thermal expansion of the components.

Looking next at FIGS. 6, 8, 19-22 and 23-25, collimator support 120 supports collimator 125 relative to X-ray tube 100 and heat sink 115, with collimator opening 205 (FIG. 25) aligned with window 185 (FIGS. 16 and 17) of heat sink 115 (and hence with emitter opening 150 of X-ray tube 110). More particularly, an arm 210 of collimator support 120 is received in front recess 190 of heat sink 115, with a base 215 (FIGS. 23 and 24) of collimator support 120 being received in a recess 220 (FIGS. 19 and 20) of mount 100. As a result of this construction, collimator opening 205 is kept in alignment with window 185 of heat sink 115 and hence in alignment with emitter opening 150 of X-ray tube 110, so that collimator 125 may "focus" the X-rays emitted by X-ray tube 110 onto X-ray detector 30 (FIG. 3).

Heat sink 115 is preferably formed out of the same material as the anode of X-ray tube 110, such that heat sink 115 will thermally expand at the same rate as the anode of X-ray tube 110, thereby ensuring that window 185 of heat sink 115 remains in alignment with the anode of the X-ray tube 110 even if X-ray tube 110 gets hot and undergoes some thermal expansion. Furthermore, since collimator 125 is fixed to heat sink 115 via collimator support 120, collimator opening 205 remains aligned with window 185 of heat sink 115 even if thermal expansion causes some change in the position of window 185 of heat sink 115. Thus, by virtue of the foregoing construction, the emitter of X-ray tube 110 will remain in axial alignment with window 185 of heat sink 115 and opening 205 of collimator 125, regardless of any thermal expansion occurring among the parts.

Use

CT machine 5 is preferably used as follows. When a patient arrives at the emergency room presenting stroke-like symptoms, they are quickly scanned in the emergency room, on their gurney, using CT machine 5, which is pre-positioned in the emergency room. More particularly, CT machine 5 is raised on its gross movement mechanism 55, i.e., by actuating hydraulic actuators 65. CT machine 5 is then moved on its casters to the patient, so that the patient (while still lying on their gurney) is positioned within the center opening 20 of CT machine 5. Thereafter, hydraulic apparatus 65 is activated so that CT machine 5 is supported on its fine movement mechanism 60 (i.e., the centipede belt drives). Scanning is then commenced, with fine movement mechanism 60 precision-advancing CT machine 5 relative to the patient during scanning. As this occurs, heat generated by X-ray tube 110 during scanning is quickly and efficiently dissipated by the X-ray tube assembly 25, due to the unique construction of the monoblock assembly.

Application To Other Types Of Scanning Systems

It should be appreciated that the present invention is not limited to use in medical applications or, indeed, to use with CT machines. Thus, for example, the present invention may be used in connection with CT machines used for non-medical applications, e.g., with CT machines which are used to scan inanimate objects. Furthermore, the present invention may be used with non-CT-type scanning systems. In essence, the present invention has application to any X-ray based device which requires simple and effective cooling of the X-ray tube.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A system for cooling an X-ray tube in a CT machine, wherein the X-ray tube is of the type comprising a rear cylindrical portion, a front cylindrical portion, an annular face formed at the intersection of the rear cylindrical portion and the front cylindrical portion, and an emitter opening formed in the front cylindrical portion for emitting X-rays from the X-ray tube, the system comprising:
    a heat sink for drawing heat away, from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and
    a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;
    the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

2. A system according to claim 1 wherein the heat sink further comprises a front cylindrical portion, a rear cylindrical portion terminating, in an end surface, an annular face formed at the intersection of the front cylindrical portion and the rear cylindrical portion, and further wherein the end surface of the heat sink is in engagement with the annular face of the X-ray tube when the heat sink window is aligned with the emitter opening of the X-ray tube.

3. A system according to claim 1 wherein the heat sink further comprises a plurality of openings formed in the body of the heat sink.

4. A system according to claim 3 wherein the plurality of openings comprise a plurality of circumferential slots and a plurality of radial slots.

5. A system according to claim 1 further comprising a collimator support for securing the collimator to the heat sink.

6. A system according to claim 5 wherein the heat sink further comprises a front recess for receiving a portion of the collimator support.

7. An X-ray tube assembly comprising:
    an X-ray tube comprising:
        a rear cylindrical portion;
        a front cylindrical portion;
        an annular face formed at the intersection of the rear cylindrical portion and the front cylindrical portion; and
        an emitter opening formed in the front cylindrical portion for emitting X-rays from the X-ray tube; and
    a system for cooling the X-ray tube in a CT machine, the system comprising:
        a heat sink for drawing heat away from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and
        a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;
        the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

8. An assembly according to claim 7 wherein the heat sink further comprises a front cylindrical portion, a rear cylindrical portion terminating in an end surface, an annular face formed at the intersection of the front cylindrical portion and the rear cylindrical portion, and further wherein the end surface of the heat sink is in engagement with the annular face of the X-ray tube when the heat sink window is aligned with the emitter opening of the X-ray tube.

9. An assembly according to claim 7 wherein the heat sink further comprises a plurality of openings formed in the body of the heat sink.

10. An assembly according to claim 9 wherein the plurality of openings comprise a plurality of circumferential slots and a plurality of radial slots.

11. An assembly according to claim 7 further comprising a collimator support for securing the collimator to the heat sink.

12. An assembly according to claim 11 wherein the heat sink further comprises a front recess for receiving a portion of the collimator support.

13. An assembly according to claim 7 wherein the assembly further comprises a mount for supporting the X-ray tube, the heat sink and the collimator.

14. An assembly according to claim 7 wherein the mount comprises an alignment keyway, wherein the X-ray tube comprises an alignment keyway, and wherein the assembly further comprises an alignment pin for aligning the alignment keyway of the mount with the alignment keyway of the X-ray tube.

15. An anatomical imaging system comprising:
    a CT machine; and
    a transport mechanism mounted to the base of the CT machine, wherein the transport mechanism comprises a fine movement mechanism for moving the CT machine precisely, relative to the patient, during scanning;
    wherein the CT machine comprises:
        an X-ray tube assembly comprising:
            an X-ray tube comprising:
                a rear cylindrical portion;
                a front cylindrical portion;
                an annular face formed at the intersection of the rear cylindrical portion and the front cylindrical portion; and an emitter opening formed in the front cylindrical portion for emitting X-rays from the X-ray tube; and a system for cooling the X-ray tube in a CT machine, the system comprising:

a heat sink for drawing heat away from the X-ray tube, the heat sink comprising an annular body having an axial opening, and a window extending radially through the annular body, the heat sink being configured to receive the front cylindrical portion of the X-ray tube within the axial opening of the heat sink, with the emitter opening of the X-ray tube being aligned with the heat sink window; and a collimator connected to the heat sink and adapted to collimate the X-rays emitted by the X-ray tube and "focus" those X-rays on an X-ray detector, the collimator comprising a collimator opening, with the collimator being connected to the heat sink such that the collimator opening is aligned with the heat sink window and the emitter opening of the X-ray tube;

the heat sink body being formed out of the same material as the emitter of the X-ray tube, such that the emitter opening of the X-ray tube will remain aligned with both the heat sink window and the collimator opening even when the emitter of the X-ray tube undergoes thermal expansion.

16. A system according to claim 15 wherein the heat sink further comprises a front cylindrical portion, a rear cylindrical portion terminating in an end surface, an annular face formed at the intersection of the front cylindrical portion and the rear cylindrical portion, and further wherein the end surface of the heat sink is in engagement with the annular face of the X-ray tube when the heat sink window is aligned with the emitter opening of the X-ray tube.

17. A system according to claim 15 wherein the heat sink further comprises a plurality of openings formed in the body of the heat sink.

18. A system according to claim 17 wherein the plurality of openings comprise a plurality of circumferential slots and a plurality of radial slots.

19. A system according to claim 15 further comprising a collimator support for securing the collimator to the heat sink.

20. A system according to claim 19 wherein the heat sink further comprises a front recess for receiving a portion of the collimator support.

21. A system according to claim 15 wherein the assembly further comprises a mount for supporting the X-ray tube, the heat sink and the collimator.

22. A system according to claim 15 wherein the mount comprises an alignment keyway, wherein the X-ray tube comprises an alignment keyway, and wherein the assembly further comprises an alignment pin for aligning the alignment keyway of the mount with the alignment keyway of the X-ray tube.

* * * * *